United States Patent
Bandara et al.

(10) Patent No.: US 11,981,557 B2
(45) Date of Patent: May 14, 2024

(54) OHMIC NANOPORE FABRICATION AND REAL-TIME CLEANING

(71) Applicants: Southern Methodist University, Dallas, TX (US); University of Rhode Island Board of Trustees, Kingston, RI (US)

(72) Inventors: Y. M. Nuwan D. Y. Bandara, Canberra (AU); Buddini I. Karawdeniya, Canberra (AU); Jugal Saharia, Dallas, TX (US); Min Jun Kim, Plano, TX (US); Jason Rodger Dwyer, Providence, RI (US)

(73) Assignee: SOUTHERN METHODIST UNIVERSITY, Dallas, TX (US)

( * ) Notice: Subject to any disclaimer, the term of this patent is extended or adjusted under 35 U.S.C. 154(b) by 494 days.

(21) Appl. No.: 17/232,624

(22) Filed: Apr. 16, 2021

(65) Prior Publication Data
US 2021/0325329 A1   Oct. 21, 2021

Related U.S. Application Data

(60) Provisional application No. 63/011,512, filed on Apr. 17, 2020.

(51) Int. Cl.
| | |
|---|---|
| *B81B 1/00* | (2006.01) |
| *B82Y 15/00* | (2011.01) |
| *B82Y 40/00* | (2011.01) |
| *C25F 3/02* | (2006.01) |
| *G01N 27/12* | (2006.01) |
| *G01N 33/487* | (2006.01) |

(52) U.S. Cl.
CPC .............. *B81B 1/002* (2013.01); *B82Y 40/00* (2013.01); *C25F 3/02* (2013.01); *G01N 27/127* (2013.01); *G01N 33/48721* (2013.01); *B01J 2219/00864* (2013.01); *B82Y 15/00* (2013.01)

(58) Field of Classification Search
None
See application file for complete search history.

(56) References Cited

U.S. PATENT DOCUMENTS

| 9,777,389 B2 | 10/2017 | Kwok et al. |
| 9,777,390 B2 | 10/2017 | Godin et al. |
| 10,526,218 B2 | 1/2020 | Paik et al. |

OTHER PUBLICATIONS

Anderson, B. N.; et al., A., "pH tuning of DNA translocation time through organically functionalized nanopores," ACS Nano 2012, 7 (2), 1408-1414.
Ando, G.; et al., "Directly observing the motion of DNA molecules near solid-state nanopores," ACS Nano 2012, 6 (11), 10090-10097.
Asatekin, A., et al., "Polymeric nanopore membranes for hydrophobicity-based separations by conformal initiated chemical vapor deposition," Nano Letters 2010, 11 (2), 677-686.
Astier, Y., "Toward single molecule DNA sequencing: direct identification of ribonucleoside and deoxyribonucleoside 5-monophosphates by using an engineered protein nanopore equipped with a molecular adapter," Journal of the American Chemical Society 2006, 128 (5), 1705-1710.
D.Y. Bandara, Y. M. N., et al., "Characterization of Flagellar Filaments and Flagellin through Optical Microscopy and Label-Free Nanopore Responsiveness," Analytical Chemistry 2019, 91 (21), 13665-13674.
Beamish, E.; et al., "Precise control of the size and noise of solid-state nanopores using high electric fields," Nanotechnology 2012, 23 (40), 405301.
Bowden, R., et al., "Sequencing of human genomes with nanopore technology," Nat. Commun. 2019, 10 (1), 1869.
Branton, D., et al., "The potential and challenges of nanopore sequencing. In Nanoscience and Technology: A Collection of Reviews from Nature Journals," World Scientific: 2010; pp. 261-268.
Briggs, K., et al., "Automated fabrication of 2-nm solid-state nanopores for nucleic acid analysis, " Small 2014, 10 (10), 2077-2086.
Briggs, K., et al., "DNA translocations through nanopores under nanoscale preconfinement," Nano Letters 2017, 18 (2), 660-668.
Charron, M.; Briggs, K.; King, S.; Waugh, M.; Tabard-Cossa, V., "Precise DNA Concentration Measurements with Nanopores by Controlled Counting," Analytical Chemistry, Aug. 23, 2019, vol. 91, pp. 12228-12237.
Chen, P., et al., "Atomic layer deposition to fine-tune the surface properties and diameters of fabricated nanopores," Nano Letters 2004, 4 (7), 1333-1337.
Cressiot, B.; et al., "Protein transport through a narrow solid-state nanopore at high voltage: experiments and theory," ACS Nano 2012, 6 (7), 6236-6243.
Darvish, A., et al., Mechanical characterization of HIV-1 with a solid-state nanopore sensor. Electrophoresis 2018.
Dwyer, J.; Bandara, Y.; Whelan, J.; Karawdeniya, B.; Nichols, J., Silicon Nitride Thin Films for Nanofluidic Device Fabrication. Nanofluidics, 2nd Ed., RSC Nanoscience & Nanotechnology 2016, No. 41, 190-236.
Karawdeniya, B. I.; Bandara, Y. N. D.; Nichols, J. W.; Chevalier, R. B.; Hagan, J. T.; Dwyer, J. R.; "Challenging Nanopores with Analyte Scope and Environment," Journal of Analysis, Feb. 19, 2019, 3 (1), 61-79.

(Continued)

*Primary Examiner* — J. Christopher Ball
(74) *Attorney, Agent, or Firm* — Edwin S. Flores; Daniel J. Chalker; Chalker Flores, LLP

(57) ABSTRACT

The present invention includes one or more nanopores in a $Si_xN_y$ membrane comprising a monoprotic surface termination, methods of making, and methods of using the one or more nanopores, where the one or more nanopores are a chemically-tuned controlled dielectric breakdown (CT-CDB) nanopore membrane, wherein the CT-CDB allows for long-term stability of measurements in the presence of only electrolyte (open pore current stability) and ability to support many molecular detection events. In addition, the CT-CBD has pore that unclog spontaneously, in response to voltage cessation or application, or both.

20 Claims, 13 Drawing Sheets

(56) References Cited

OTHER PUBLICATIONS

Bandara, Y. N.; Karawdeniya, B. I.; Hagan, J.; Chevalier, R.; Dwyer, J. R., Chemically Functionalizing Controlled Dielectric Breakdown Silicon Nitride Nanopores by Direct Photohydrosilylation. ACS Appl. Mater. Interfaces Jul. 26, 2019, pp. 30411-30420.

Bandara, Y. N. D.; Karawdeniya, B. I.; Dwyer, J. R., Push-Button Method to Create Nanopores Using a Tesla-Coil Lighter. ACS Omega, Jan. 4, 2019, 4 (1), 226-230.

Firnkes, M.; et al., "Electrically facilitated translocations of proteins through silicon nitride nanopores: conjoint and competitive action of diffusion, electrophoresis, and electroosmosis," Nano Lett. May 30, 2010, 10 (6), 2162-2167.

Freedman, K. J.; et al., Detection of long and short DNA using nanopores with graphitic polyhedral edges. ACS Nano May 28, 2013, 7 (6), 5008-5016.

Freedman, K. J.; et al., Chemical, thermal, and electric field induced unfolding of single protein molecules studied using nanopores. Anal. Chem. May 11, 2011, 83 (13), 5137-5144.

Graf, M.; et al.; Radenovic, A., Transverse Detection of DNA in a MoS2 Nanopore. Nano Letters, Nov. 11, 2019, 19, 9075-9083.

Han, A.; et al., "Sensing protein molecules using nanofabricated pores," Appl. Phys. Lett. Jan. 18, 2006, 88 (9), 093901.

Hoogerheide, D. P.; et al., Probing surface charge fluctuations with solid-state nanopores. Physical review letters Jun. 26, 2009, 102 (25), 256804.

Karawdeniya, B. I.; Bandara, Y. N. D.; Nichols, J. W.; Chevalier, R. B.; Dwyer, J. R., Surveying silicon nitride nanopores for glycomics and heparin quality assurance. Nat. Commun. Aug. 16, 2018, 9 (1), 1-8.

Karawdeniya, B. I.; Bandara, Y. N. D.; Nichols, J. W.; Chevalier, R. B.; Hagan, J. T.; Dwyer, J. R.; Testing, Challenging Nanopores with Analyte Scope and Environment. Journal of Analysis, Feb. 19, 2019, 3 (1), 61-79.

Kasianowicz, J. J.; Brandin, E.; Branton, D.; Deamer, D. W., Characterization of individual polynucleotide molecules using a membrane channel. Proceedings of the National Academy of Sciences, Nov. 1996, vol. 93 (24), 13770-13773.

Kwok, H.; Briggs, K.; Tabard-Cossa, V., "Nanopore fabrication by controlled dielectric breakdown," PLoS One Mar. 2014, 9 (3), e92880.

Lee, J. S.; et al., Stiffness measurement of nanosized liposomes using solid-state nanopore sensor with automated recapturing platform. Electrophoresis 2019, 40 (9), 1337-1344.

Plesa, C.; et al.,, Fast translocation of proteins through solid state nanopores. Nano Lett. Jan. 23, 2013, 13 (2), 658-63.

Saharia, J.; et al., Molecular-Level Profiling of Human Serum Transferrin Protein through Assessment of Nanopore-Based Electrical and Chemical Responsiveness. ACS Nano Mar. 7, 2019, 13 (4), 4246-4254.

Singer, A.; et al., Detection of urea-induced internal denaturation of dsDNA using solid-state nanopores. J. Phys.: Condens. Matter Oct. 29, 2010, 22 (45), 454111.

Venta, K.; et al., Differentiation of short, single-stranded DNA homopolymers in solid-state nanopores. ACS Nano Apr. 26, 2013, 7 (5), 4629-4636.

Yanagi, I.; et al., Stable fabrication of a large nanopore by controlled dielectric breakdown in a high-pH solution for the detection of various-sized molecules. Scientific Reports Sep. 11, 2019, 9 (1), 1-15.

Yusko, E. C.; et al., Controlling protein translocation through nanopores with bio-inspired fluid walls. Nature Nanotechnolagy Feb. 20, 2011, 6 (4), 253-260.

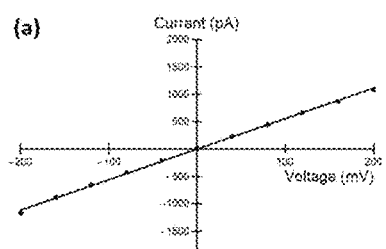 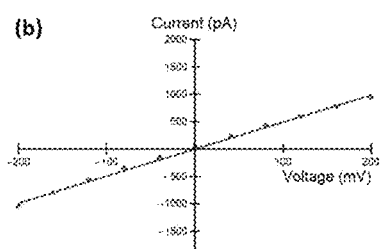 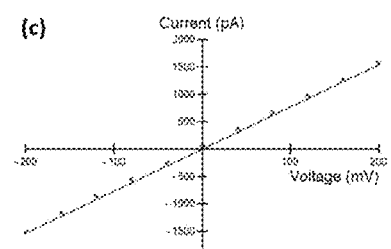
FIG. 1A  FIG. 1B  FIG. 1C
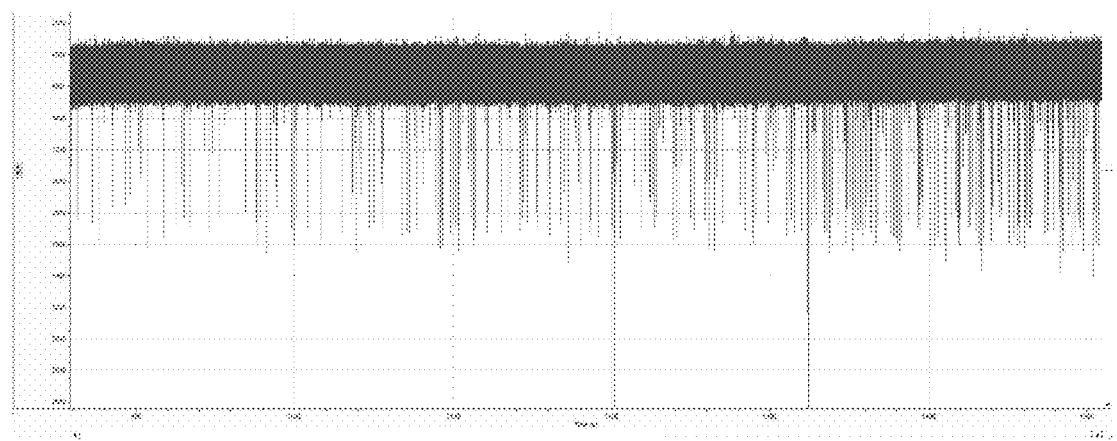
FIG. 2

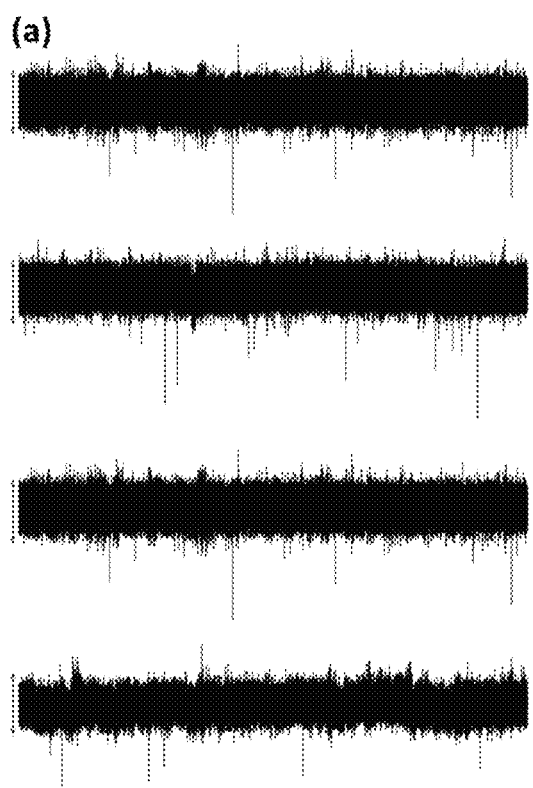
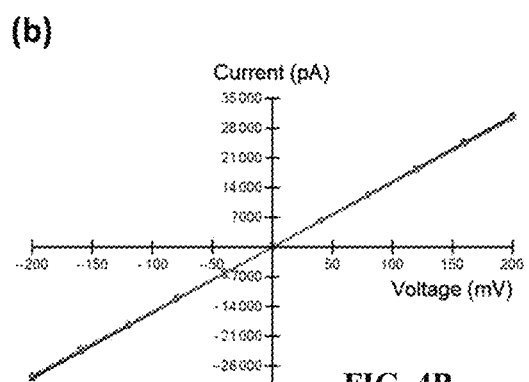
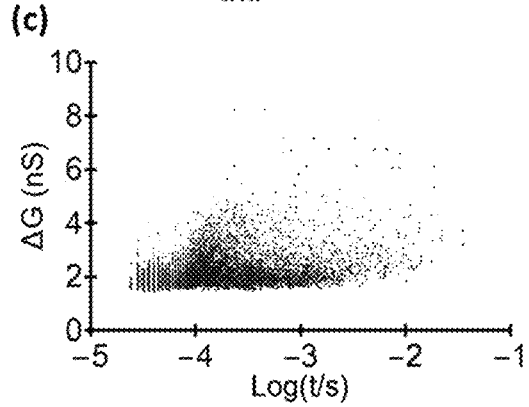
FIG. 4A
FIG. 4B
FIG. 4C

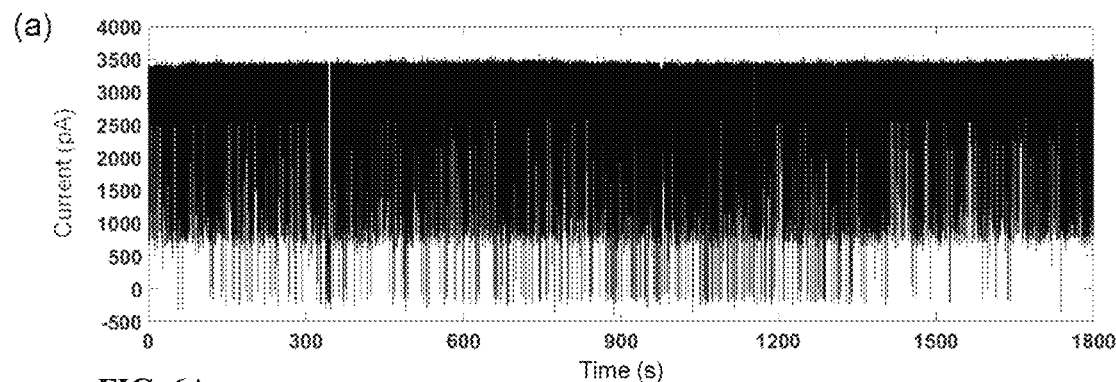
FIG. 6A
FIG. 6B
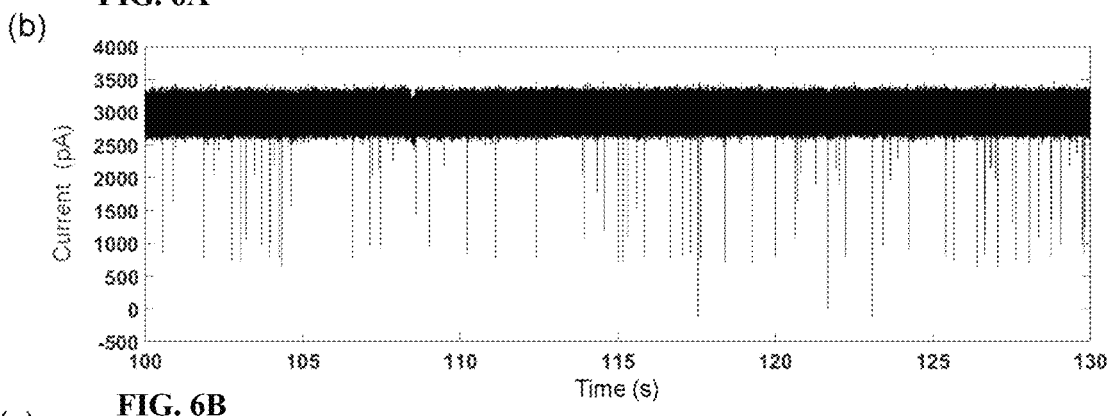
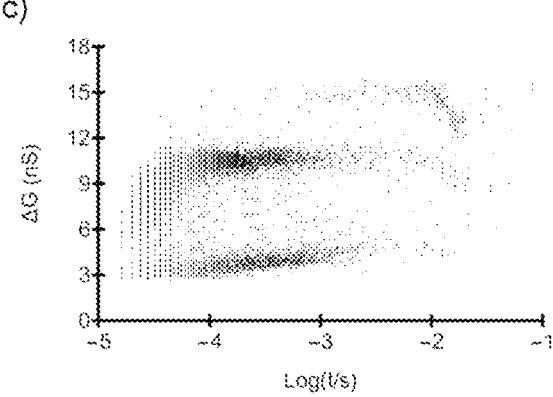
FIG. 6C
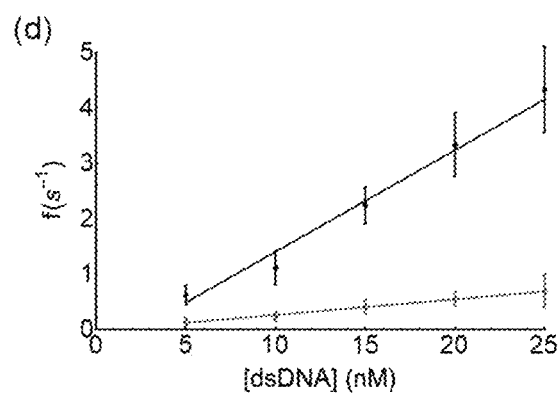
FIG. 6D

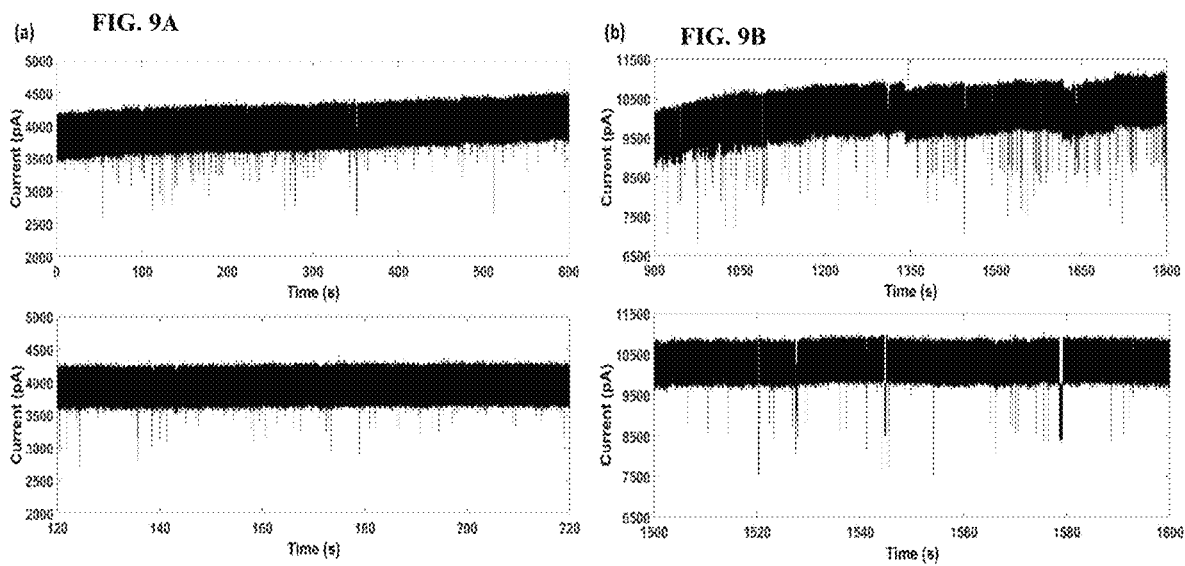

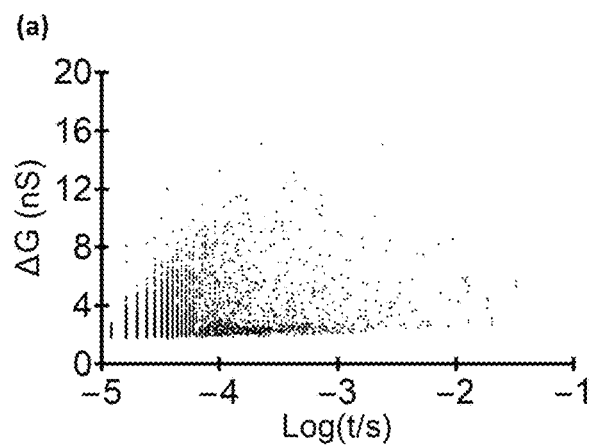
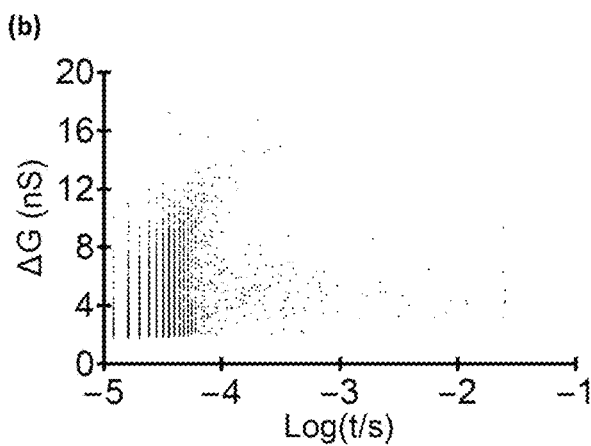
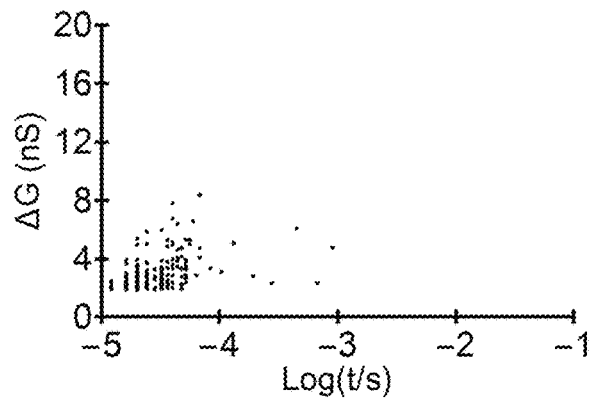
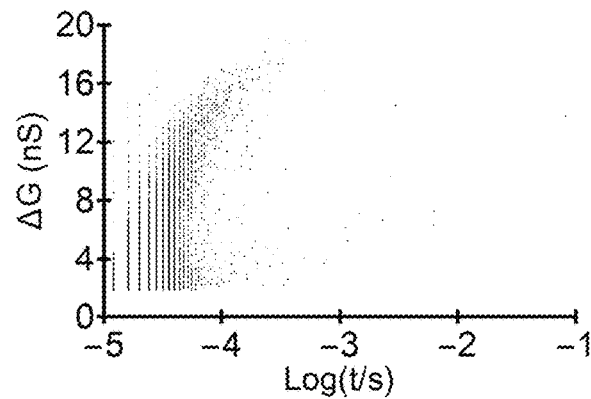
FIG. 13A
FIG. 13B

OHMIC NANOPORE FABRICATION AND REAL-TIME CLEANING

CROSS-REFERENCE TO RELATED APPLICATIONS

This application claims priority to U.S. Provisional Patent Application Ser. No. 63/011,512 filed on Apr. 17, 2020 entitled Ohmic Nanopore Fabrication and Real-Time Cleaning, the entire contents of which are hereby incorporated by reference.

STATEMENT OF FEDERALLY FUNDED RESEARCH

This invention was made with government support under CMMI1707818, CMMI1712069, CHE1808344, and CBET1150085 awarded by the National Science Foundation, and R03EB022759 awarded by the National Institutes of Health. The government has certain rights in the invention.

TECHNICAL FIELD OF THE INVENTION

The present invention relates in general to the field of improved devices, methods of making and using systems for real-time cleaning and fabrication of instantaneously Ohmic nanopores for improved reusability.

BACKGROUND OF THE INVENTION

Without limiting the scope of the invention, its background is described in connection with nanopores and nanopore fabrication.

Solid-state nanopores (SSNs) are single-molecule resolution sensors with a growing footprint in real-time biopolymer profiling-most prominently, but far from exclusively, DNA sequencing. SSNs accessibility has increased with the advent of controlled dielectric breakdown (CDB), but severe fundamental challenges remain: drifts in open-pore current and irreversible analyte sticking. Unfortunately, these behaviors impede on-going basic research and device development for commercial applications, which are dramatically exacerbated by the chemical complexity and physical property diversity of different analytes.

Nanopores are nanofluidic channels through impervious membranes. Single molecules translocating through suitably sized nanopores filled with electrolyte can displace ions to generate resistive pulses stamped with analyte-specific information[1,2] Nanopores have seen extensive development over decades in pursuit of better performance, with DNA sequencing being the most conspicuous example. The promise of these nanofluidic tools transcends DNA and RNA sequencing to encompass the sequencing, mapping, and characterization—as simple as sizing—also of proteins and glycans, so that nanopores have the potential to have a profound effect on the biopolymer characterization so vital to genomics, proteomics, and glycomics.[3-5] Work with protein nanopores has been foundational and continues to drive advances,[6,7] but solid-state nanopores (SSNs) have nevertheless long remained a target of nanopore science. SSNs are mechanically robust, size-tunable, and the popular silicon nitride ($SiN_x$) offers reliable nanofabrication workflow compatibility.[2] Such nanopores offer the capability for performing nanopore force spectroscopy across a usefully wide range of forces and ensure that linear, folded, and branched polymers, as well as nanoparticles and bioparticles such as exosomes, can all be within reach of this technology.[3, 8-11] The difficulties of reproducible and accessible fabrication of small (~1-10 nm diameter) nanopores remains a challenge of SSN development and has limited the rate of its adoption and advance in applications.

Controlled dielectric breakdown (CDB) devices have brought some simplicity, low-cost, and efficiency to SSN fabrication,[12] however, significant barriers to reliable use of $SiN_x$ SSNs remain, including: delayed wetting, instability in the open pore current, (irreversible) analyte "sticking" that causes signal perturbations and can lead to clogging, and complex, often problematic native surface chemistry. The frequent need for ad hoc approaches to ameliorate these issues has become a largely accepted part of nanopore science, as a legacy of fabrication challenges, alone, but also in testament to the promise of the tool. Highly specialized solutions to prevent sticking by particular molecules within a particular analyte class exist but can introduce cost or change the nanopore properties too much.[13] Similarly, post-fabrication modification of $SiN_x$ nanopores with organic films has been demonstrated,[14] but physical flexibility of the film constituents and interactions with solution components creates a complex interface, as seen in the charge adsorption by the very PEG molecules often used for surface passivation. To date, no straightforward general method for suppressing nanopore sticking using an inorganic layer integral to the as-fabricated nanopore surface has been demonstrated.

One such patent is U.S. Pat. No. 10,526,218, issued to Paik, et al., entitled, "Flow control method and apparatuses". This patent is said to teach a device to measure the flow of analytes, particles or other materials. The device includes a membrane having one or more pores in a membrane, electrodes that facilitate electrophoretic flow of analytes through the pore, and a third electrode the controls the movement of particles in the pore by modulating the shape of an electric double layer adjacent sidewalls of pore. This modulation is said to control the strength of an electro-osmotic field that opposes the electrophoretic flow of the analytes via the pore.

Another such patent is U.S. Pat. No. 9,777,390, issued to Godin, et al., entitled "Method for controlling the size of solid-state nanopores". These inventors are said to teach a method for precisely enlarging a nanopore formed in a membrane that includes: applying an electric potential across the nanopore, where the electric potential has a pulsed waveform oscillating between a high value and a low value; measuring current flowing though the nanopore while the electric potential is being applied to the nanopore at a low value; determining size of the nanopore based in part on the measured current; and removing the electric potential applied to the membrane when the size of the nanopore corresponds to a desired size.

Another such patent is U.S. Pat. No. 9,777,389, issued to Kwok, et al., entitled "Fabrication of nanopores using high electric fields." These inventors are said to teach a method for fabricating a nanopore in a membrane by applying an electric potential across the membrane, where value of the electric potential is selected to induce an electric field which causes a leakage current across the membrane; monitoring current flow across the membrane while the electric potential is being applied; detecting an abrupt increase in the leakage current across the membrane; and removing the electric potential across the membrane in response to detecting the abrupt increase in the leakage current.

What is needed is are novel devices, methods of making, and methods of using and cleaning SSNs that provide robust signal acquisition and reproducibility, that are self-cleaning and that allow for long-term, stable measurements across the membrane.

SUMMARY OF THE INVENTION

In one embodiment, the present invention includes a method of making a controlled-size nanopore in a membrane comprising: providing a $Si_xN_y$ membrane; submerging the $Si_xN_y$ membrane in a buffered solution comprising Group IA-Cl or F: Group IA-hypochlorite in the presence of less than or equal to 1 V/nm of transmembrane electric field strength. In one aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores in the membrane are unclogged by adding or removing an applied voltage across the nanopores. In another aspect, the Group IA-Cl or F is buffered prior to the addition of the hypochlorite. In another aspect, the Group IA-Cl salt is selected from LiCl, NaCl, KCl, RbCl, CsCl, LiF, NaF, KF, RbF, CsF, LiBr, NaBr, KBr, RbBr, or CsBr. In another aspect, the Group IA-hypochlorite is selected from LiOCl, NaOCl, KOCl, RbOCl, or CsOCl. In another aspect, the membrane has one nanopore. In another aspect, the method further comprises adjusting the voltage, or a time, to create nanopores having an average diameter of about 4, 5, 6, 7, 8, 9, 10, 12, 14, 15, 17, 20, or 25 nm. In another aspect, the electric field strength was set to <0.7, 0.8, or 0.9 V/nm. In another aspect, the method further comprises rectifying the fabricated nanopores as a ratio of conductance at positive voltage regime (G+) to that at negative voltage regime (G−): G+/G−. In another aspect, the electrical signals are obtained using silver, Ag/AgCl, gold, carbon, or platinum electrodes, or combinations thereof. In another aspect, the one or more nanopores are clog-resistant.

In another embodiment, the present invention includes a chemically-tuned controlled dielectric breakdown (CT-CDB) nanopore membrane comprising: an $Si_xN_y$ membrane wherein a surface at or about one or more nanopores in the $Si_xN_y$ membrane comprise a monoprotic surface termination. In one aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores have an average diameter of about 4, 5, 6, 7, 8, 9, 10, 12, 14, 15, 17, 20, or 25 nm. In another aspect, the one or more nanopores are formed with an electric field strength was set to <0.7, 0.8, or 0.9 V/nm. In another aspect, the one or more nanopores are clog-resistant. In another aspect, the nanopores in the membrane are uncloggable by removal or adding an applied voltage. In another aspect, the membrane has one nanopore.

In yet another embodiment, the present invention includes a method of detecting an analyte, comprising: providing a first chamber and a second chamber, wherein the first and second chamber are separated by an $Si_xN_y$ membrane wherein a surface at or about one or more nanopores in the $Si_xN_y$ membrane comprise a monoprotic surface termination; placing the analyte in the first or second chamber; applying a voltage across the $Si_xN_y$ membrane; and detecting the analyte as it contacts or traverses the $Si_xN_y$ membrane. In one aspect, the analytes are selected from nucleic acids, proteins, carbohydrates, small molecules, lipids, viruses, liposomes, or nanoparticles. In another aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores have an average diameter of about 4, 5, 6, 7, 8, 9, 10, 12, 14, 15, 17, 20, or 25 nm. In another aspect, the one or more nanopores are formed with an electric field strength was set to <0.7, 0.8, or 0.9 V/nm. In another aspect, the electrical signals are obtained using silver, Ag/AgCl, gold, carbon, or platinum electrodes, or combinations thereof. In another aspect, the one or more nanopores are clog-resistant. In another aspect, the one or more nanopores in the membrane are unclogged by adding or removing an applied voltage across the $Si_xN_y$ membrane. In another aspect, the membrane has one nanopore.

In another embodiment, the present invention includes an apparatus comprising: a membrane having at least one controlled-size nanopores in a membrane between opposing surfaces of the membrane, wherein the membrane is a chemically-tuned controlled dielectric breakdown (CT-CDB) nanopore membrane comprising: an $Si_xN_y$ membrane wherein a surface at or about one or more nanopores in the $Si_xN_y$ membrane comprise a monoprotic surface termination; a first reservoir and a second reservoir on opposite sides of the at least one controlled-size nanopores of the membrane; a first and a second electrodes arranged on opposite sides of the fluidic pore of the membrane; and a controller connected to each of the first and second electrodes and a sensor in fluid communication with at least one of the first and second reservoirs.

A method is provided for tuning a nanopore formed in a solid-state membrane, wherein the membrane is made by providing a $Si_xN_y$ membrane; submerging the $Si_xN_y$ membrane in a buffered solution comprising Group IA-Cl or F: Group IA-hypochlorite in the presence of less than or equal to 1 V/nm of transmembrane electric field strength. In one aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores in the membrane are unclogged by adding or removing an applied voltage across the nanopores. In another aspect, the Group IA-Cl or F is buffered prior to the addition of the hypochlorite. In another aspect, the Group IA-Cl salt is selected from LiCl, NaCl, KCl, RbCl, CsCl, LiF, NaF, KF, RbF, CsF, LiBr, NaBr, KBr, RbBr, or CsBr. In another aspect, the Group IA-hypochlorite is selected from LiOCl, NaOCl, KOCl, RbOCl, or CsOCl. In another aspect, the membrane has one nanopore. In another aspect, the method further comprises adjusting the voltage, or a time, to create nanopores having an average diameter of about 4, 5, 6, 7, 8, 9, 10, 12, 14, 15, 17, 20, or 25 nm. In another aspect, the electric field strength was set to <0.7, 0.8, or 0.9 V/nm. In another aspect, the method further comprises rectifying the fabricated nanopores as a ratio of conductance at positive voltage regime (G+) to that at negative voltage regime (G−): G+/G−. In another aspect, the electrical signals are obtained using silver, Ag/AgCl, gold, carbon, or platinum electrodes, or combinations thereof. In another aspect, the one or more nanopores are clog-resistant. applying an electric potential across the nanopore, where the electric potential has a pulsed waveform oscillating between a high value and a low value; measuring current flowing through the nanopore; determining size of the nanopore based in part on the measured current; and removing the electric potential applied across the nanopore when the size of the nanopore corresponds to a desired size.

In another aspect of the disclosure, measuring of the current flowing through the nanopore occurs while the electric potential is being applied at a high value; whereas, in another aspect, measuring of the current flowing through the nanopore occurs while the electric potential is being applied at a low value, wherein the membrane has at least one controlled-size nanopore in a membrane between opposing surfaces of the membrane, wherein the membrane is a chemically-tuned controlled dielectric breakdown (CT-CDB) nanopore membrane comprising: an $Si_xN_y$ membrane wherein a surface at or about one or more nanopores in the $Si_xN_y$ membrane comprise a monoprotic surface termination; a first reservoir and a second reservoir on opposite sides of the at least one controlled-size nanopores of the membrane; a first and a second electrodes arranged on opposite sides of the fluidic pore of the membrane; and a controller connected to each of the first and second electrodes and a sensor in fluid communication with at least one of the first and second reservoirs.

In some aspects of the disclosure, this process is repeated until the measured current exceeds a threshold. When reapplying relatively high electric potential, the polarity of the electric potential may be reversed to achieve or maintain symmetry in pore geometry, wherein membrane is made by providing a $Si_xN_y$ membrane; submerging the $Si_xN_y$ membrane in a buffered solution comprising Group IA-Cl or F: Group IA-hypochlorite in the presence of less than or equal to 1 V/nm of transmembrane electric field strength. In one aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores in the membrane are unclogged by adding or removing an applied voltage across the nanopores. In another aspect, the Group IA-Cl or F is buffered prior to the addition of the hypochlorite. In another aspect, the Group IA-Cl salt is selected from LiCl, NaCl, KCl, RbCl, CsCl, LiF, NaF, KF, RbF, CsF, LiBr, NaBr, KBr, RbBr, or CsBr. In another aspect, the Group IA-hypochlorite is selected from LiOCl, NaOCl, KOCl, RbOCl, or CsOCl. Once the measured current exceeds the threshold, the electric potential is removed.

A method is provided for fabricating a nanopore in a dielectric membrane immersed in a solution containing ions that is made by: providing a $Si_xN_y$ membrane; submerging the $Si_xN_y$ membrane in a buffered solution comprising Group IA-Cl or F: Group IA-hypochlorite in the presence of less than or equal to 1 V/nm of transmembrane electric field strength, and applying an electric potential across the membrane, where value of the electric potential is selected to induce an electric field which causes a leakage current across the otherwise insulating membrane; monitoring current flow across the membrane while the electric potential is being applied; detecting a sudden irreversible increase in the leakage current across the membrane; and removing the electric potential across the membrane in response to detecting the sudden increase in the leakage current to stop the fabrication of the nanopore. In one aspect, the $Si_xN_y$ membrane is nominally 5, 6, 7, 8, 9, 10, 11, 12, 13, 15, 20, 25, 30, 35, 40, 50, 60, 70, 75, 80, 90, or 100 nm. In another aspect, the one or more nanopores in the membrane are unclogged by adding or removing an applied voltage across the nanopores. In another aspect, the Group IA-Cl or F is buffered prior to the addition of the hypochlorite. In another aspect, the Group IA-Cl salt is selected from LiCl, NaCl, KCl, RbCl, CsCl, LiF, NaF, KF, RbF, CsF, LiBr, NaBr, KBr, RbBr, or CsBr. In another aspect, the Group IA-hypochlorite is selected from LiOCl, NaOCl, KOCl, RbOCl, or CsOCl. Once the measured current exceeds the threshold, the electric potential is removed.

In another embodiment, an abrupt increase in the leakage current is detected by comparing a value of the monitored current to a threshold and then ceasing to apply the electric potential when the value of the monitored current exceeds the threshold. In another aspect, the membrane is disposed between two reservoirs filled with a fluid and thereby prevents the fluid from passing between the two reservoirs.

In another embodiment, the present invention includes an apparatus that includes the membrane of the present invention. The apparatus includes: two reservoirs fluidly coupled via a passageway to each other; a pair of electrodes electrically connected to a voltage source, such that one electrode is disposed in each of the two reservoirs and the pair of electrodes generate an electric potential across the membrane; a current sensor electrically coupled to one of the electrodes and operable to measure current flowing between the two reservoirs; and a controller interfaced with the current sensor, wherein the controller detects an abrupt increase in the measured current and, in response to detecting the abrupt increase in the measured current, removes the voltage across the electrodes.

BRIEF DESCRIPTION OF THE DRAWINGS

For a more complete understanding of the features and advantages of the present invention, reference is now made to the detailed description of the invention along with the accompanying figures and in which:

FIGS. 1A to 1C show the Current-Voltage (I-V) curves of a nanopore fabricated (~3 nm in diameter) through a 12 nm thick silicon nitride membrane using 1:4.5 sodium hypochlorite (10-15%): 1M KCl (buffered at pH~7) solution. (FIG. 1A) 1M KCl, (FIG. 1B) 2M LiCl and (FIG. 1C) 4M LiCl. All electrolytes are buffered at pH~7 and I-V curves are taken soon after fabrication.

FIG. 2 is a graph that shows a >10-minute current trace of 17 nM DNA translocating through a ~4.7 nm diameter nanopore (4M LiCl buffered at pH~7) nanopore under +200 mV applied voltage.

FIGS. 4A to 4C show: FIG. 4A show a 10-second representative current traces corresponding to four separate runs of hSTf through the same ~26 nm diameter nanopore (in chronological order from top to bottom) in ~30 nm thick silicon nitride membrane. The scale bar in red represents 1 nA. Before each run, the nanopore is cleaned with the cleaning solution described in the text. The I-V curves in (FIG. 4B) corresponding to each run shows a perfect overlap and a similar observation is seen in (FIG. 4C) where scatter plots corresponding to each run also show a near-perfect overlap (run1: magenta, run2: green, run3: black and run4: blue).

(FIG. 5A) Representative I-V curves of pores (<4 nm in diameter) fabricated from the CT-CDB protocol (4 M LiCl buffered at pH~7 with HEPES). (FIG. 5B) Power spectral density (PSD, see methods for more details) noise spectra (4 M LiCl buffered at pH~7, 250 kHz acquisition rate, 100 kHz low-pass filtering) corresponding to pores fabricated from the CDB (blue, ~4.4 nm diameter) and CT-CDB protocols (magenta, ~4.8 nm diameter). Conductance as a function of pH using (1 M KCl, buffered at pH~7 with HEPES) of ~13 nm diameter nanopores fabricated from (FIG. 5C) CDB protocol and (FIG. 5D) CT-CDB. Since the pH responsiveness of the surface head groups of CT-CDB increases drastically after pH~9, the ordinates of (FIG. 5C) and (FIG. 5D) are deliberately set at different scales to better showcase the G-pH trends of each case.

FIGS. 6A to 6D show: (FIG. 6A) A ~30-minute current of 1 kb dsDNA (25 nM) translocating through a ~3.4 nm diameter CT-CDB pore in 4 M LiCl (buffered at pH~7) and (FIG. 6B) a 30-second representative current trace of (FIG. 6A) from 100 s to 130 s. The experiment was conducted over 3 hours at +200 mV of applied voltage, 250 kHz sampling rate and 100 kHz lowpass filtering. (FIG. 6C). Scatter plot (13417 events over 3 hours) showing conductance change ($\Delta G$) and the log of translocation time. (FIG. 6D) Calibration curve (inter-event frequency vs dsDNA concentration) constructed by adding 1 kb dsDNA (4M LiCl buffered at pH~7) in ~5 nM increments to ~5 nm diameter nanopores fabricated from the CDB protocol (magenta) and CT-CDB protocol (black). Each dsDNA aliquot of (FIG. 6D) was run for at least 900 seconds and each data point represents at least ~750 (CDB) and 3800 (CT-CDB) events. Data were obtained using an applied voltage of +200 mV, 250 kHz of sampling frequency and 100 kHz of low-pass filtering.

FIG. 7A to 7D shows representative 60-second current traces of maltodextrin translocation in response to +200 mV and −200 mV (current and voltage polarities are of identical sign) in pores fabricated from (FIG. 7A) and (FIG. 7B) the CDB and (FIG. 7C) and (FIG. 7D) CT-CDB protocols at pH ~7 (upper row) and ~9 (lower row). The schematic representation above the current traces summarizes the EO direction at each instance. All data were acquired at 250 kHz sampling rate, 100 kHz lowpass filtering using ~5 nm diameter pores that are nominally ~12 nm in thickness. The scatter plots corresponding to these traces are shown in FIGS. 13A and 13B.

FIGS. 8A to 8D show: (column 1) Representative 15 minute current traces originating translocation of hSTf in 4M LiCl (buffered at pH~7) under +50 mV applied voltage (100 kHz lowpass filtering, 250 kHz sampling rate) and their (column 2) corresponding heatmaps overlaid with raw-data points of conductance change as a function of translocation time of (FIG. 8A) ~12 nm diameter CT-CDB pore, (FIG. 8B) ~17 nm diameter CT-CDB pore, (FIG. 8C) ~18 nm diameter CDB pore and (FIG. 8D) ~20 nm diameter CT-CDB pore. For brevity, representative 30-second current traces of each of these pores are shown in FIGS. 14A to 14E.

FIGS. 9A and 9B show: (top row) Extended representative current traces and (bottom row) representative 100-second current traces in CDB nanopores resulting from dsDNA translocation through (FIG. 9A) ~4.6 nm and (FIG. 9B) ~6.2 nm diameter CDB nanopore. All translocation experiments were done in 4 M LiCl buffered at pH~7, 250 kHz acquisition rate, 100 kHz low-pass filtering, +200 mV applied voltage with a final dsDNA concentration of ~25 nM.

Figure 10A:
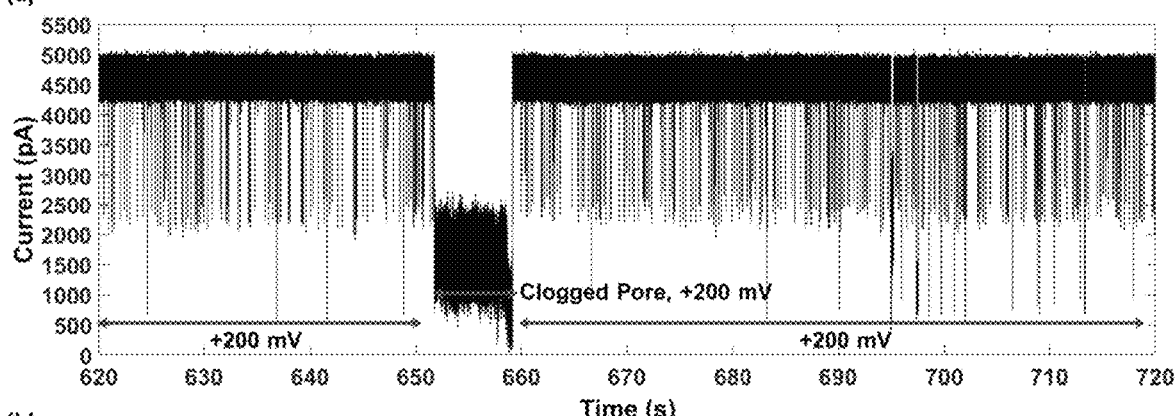
Figure 10B:
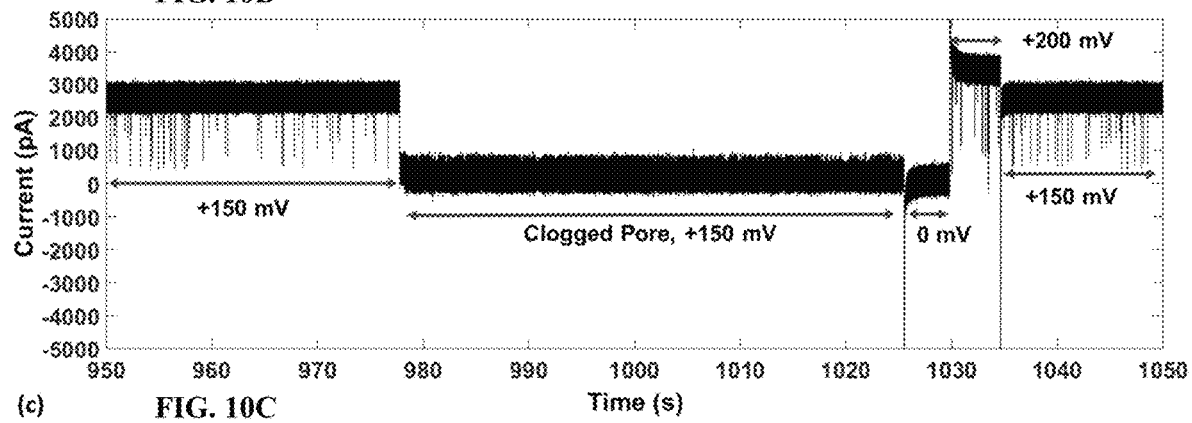
Figure 10C:
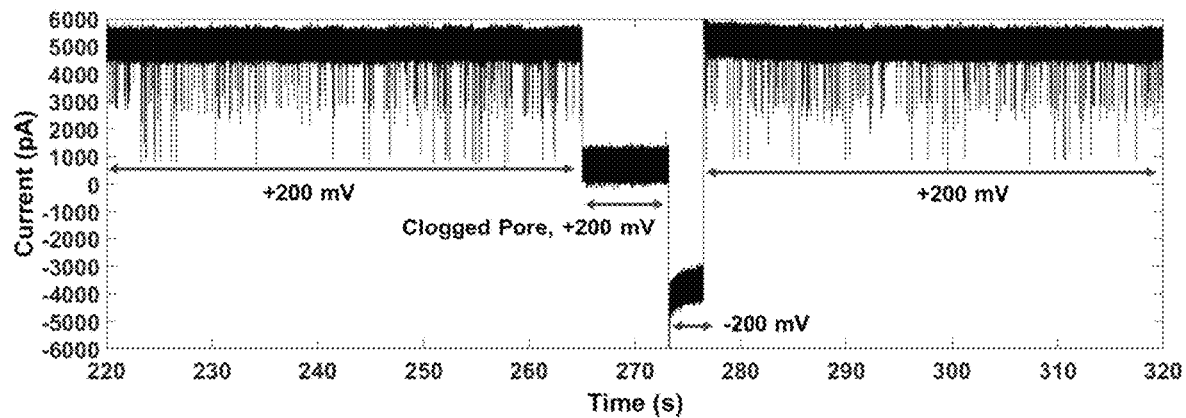

FIGS. 10A to 10C show: all translocation traces presented here are from 25 nM dsDNA in 4M LiCl buffered at pH~7 (250 kHz sampling frequency and 100 kHz lowpass filtering) through CT-CDB pores. (FIG. 10A) A ~4.9 nm pore that self corrects after an initial clog, (FIG. 10B) a ~4.0 nm diameter pore that failed to self-correct was recovered by zeroing the voltage and (FIG. 10C) a ~4.9 nm diameter pore unclogged by applying −200 mV. The baseline voltage is +200 mV except in (b) where it is +150 mV and for comparison, after unclogging the pore, it is run at +200 mV for a short while. CT-CDB pores maintained overall current level stability by spontaneous correction, and by more active interventions including temporary cessation of applied voltage, and temporary voltage polarity reversal.

Figure 11:
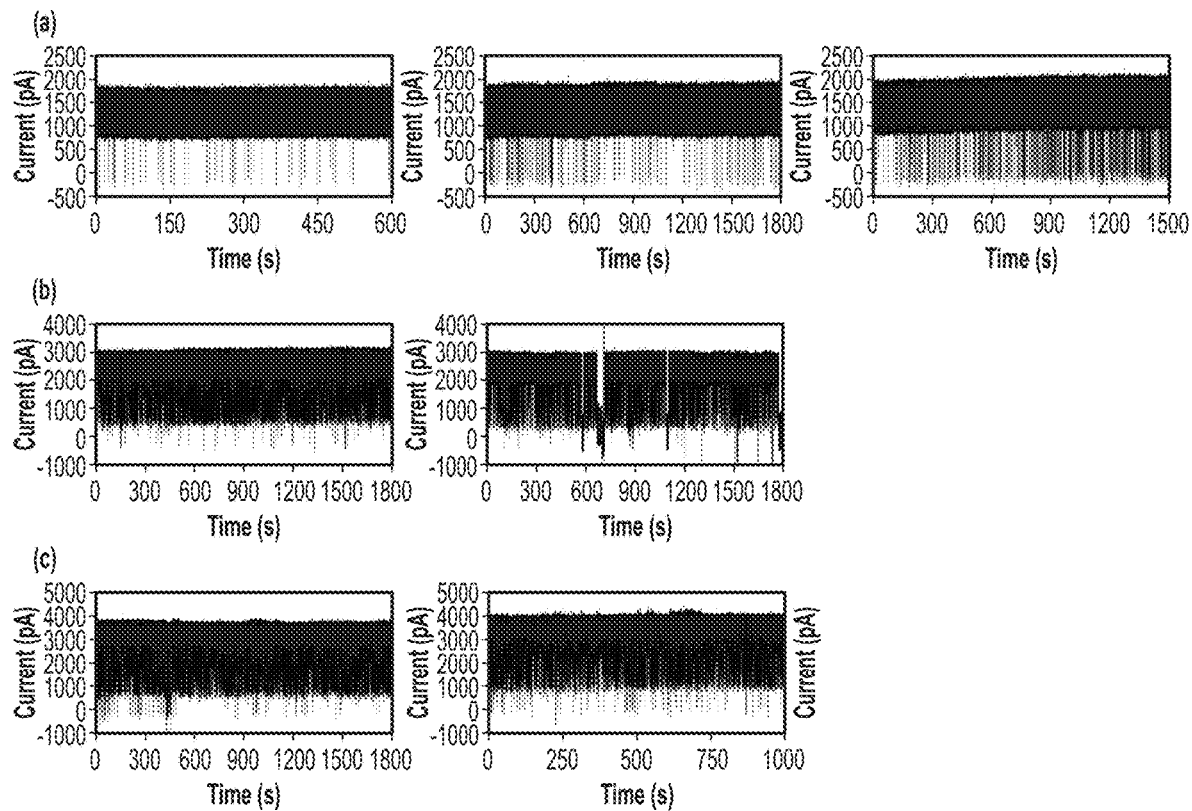

FIG. 11A to 11C show representative current traces of 4.3 nm diameter CT-CDB pore corresponding to translocation of ~25 nM dsDNA at (FIG. 11A)+100 mV, (FIG. 11B)+150 mV and (FIG. 11C)+200 mV applied voltage. All translocation experiments were done in 4M LiCl (buffered at pH ~7), 250 kHz sampling rate and 100 kHz lowpass filtering. Reversible clogging at +150 mV is equivalent to those observed in FIGS. 10A-10C.

Figure 12:
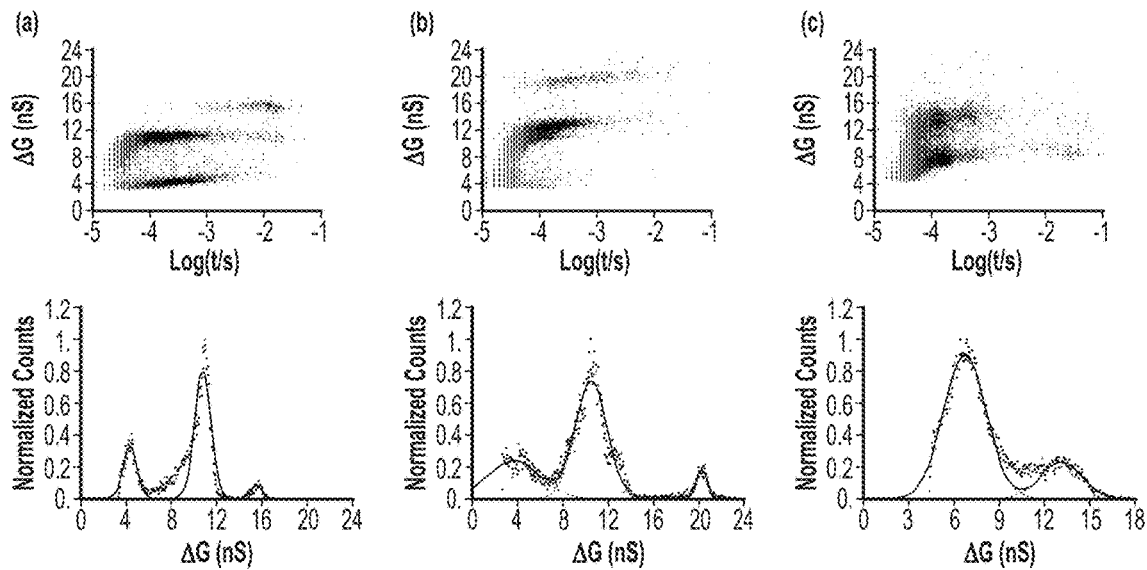

FIGS. 12A to 12C show scatter plots (1st row) and histograms of $\Delta G$ (2nd row) as a result of dsDNA translocating through (FIG. 12A) ~3.4 nm, (FIG. 12B) ~4.7 nm and (FIG. 12C) ~10.0 nm diameter CT-CDB nanopores. All translocation experiments were done in 4 M LiCl (buffered at pH ~7), +200 mV of applied voltage, 250 kHz sampling rate and 100 kHz lowpass filtering. The histograms were fitted with (a) three (b) three (c) and two Gaussian.

FIGS. 13A and 13B show scatter plots of change in conductance ($\Delta G$) vs the log of translocation time (t) corresponding maltodextrin translocating through pores fabricated from (top row) CDB and (bottom row) CT-CDB protocols. Experiments were conducted at (FIG. 13A) pH ~7 using +200 mV and (FIG. 13B) pH ~9 using +200 mV with 250 kHz sampling frequency and 100 kHz lowpass filtering.

FIGS. 14A to 14E show representative 30-second current traces of hSTf translocations through (FIG. 14A) ~11.9 nm CT-CDB pore, (FIG. 14B) 17.2 nm CT-CDB pore, (FIG. 14C) 17.9 nm CDB pore and (FIG. 14D) 20.4 nm CT-CDB pore. (FIG. 14E) Extended current trace of ~75 minutes through a ~13.8 nm CT-CDB pore. All experiments were done in 4M LiCl (buffered at pH~7) under +50 mV of applied voltage (100 kHz lowpass filtering, 250 kHz sampling rate) with ~100 nM hSTf except in (FIG. 14C) where the concentration was ~250 nM.

FIGS. 15A to 15F show histograms corresponding to the conductance change ($\Delta G$) as result of hSTf translocating through (FIG. 15A) ~11.9 nm CT-CDB pore, (FIG. 15B) ~13.8 nm CDB pore, (FIG. 15C) 17.2 nm CT-CDB pore, (FIG. 15D) 17.9 nm CDB pore, (FIG. 15E) 20.4 nm CT-CDB pore and (FIG. 15F) 27.8 nm CT-CDB pore. The inset shows the corresponding heatmaps overlaid with the scatter plots of $\Delta G$ vs translocation time. All experiments were done in 4M LiCl (buffered at pH~7) under +50 mV of applied voltage (100 kHz lowpass filtering, 250 kHz sampling rate) with ~100 nM hSTf except in (FIG. 15D) where the concentration was ~250 nM.

Figure 16A:
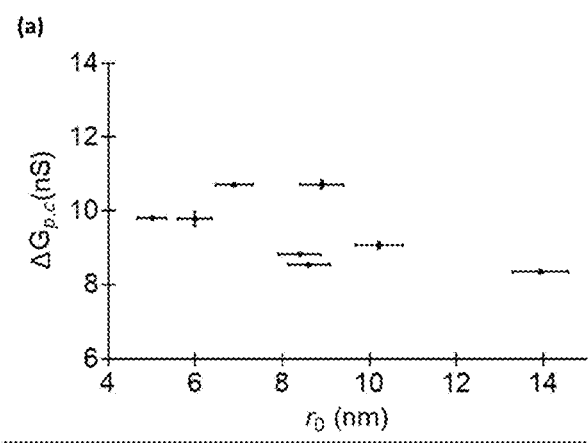
Figure 16B:
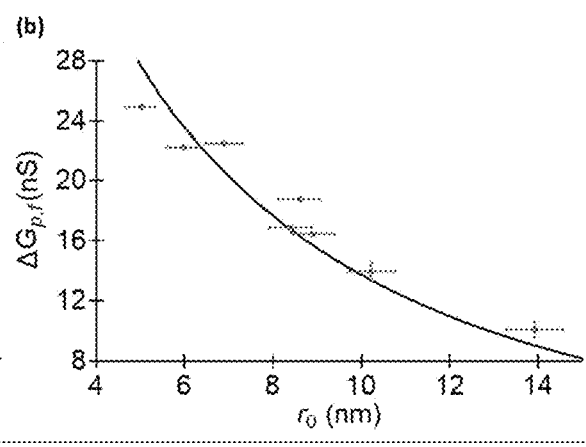

FIGS. 16A and 16B show: (FIG. 16A) ⟦$\Delta G$⟧ (p,c) and (FIG. 16B) ⟦$\Delta G$⟧ (p,f) (see section 9 for assignment) as a function of pore diameter of nanopores fabricated from the CT-CDB protocol. The vertical and horizontal error bars are the error in the Gaussian fit (3×) and error originating from membrane thickness uncertainty (±2 nm, provided by the manufacturer) respectively. The solid-line in (FIG. 16B) is a fit made using equation S6 with $\gamma \cdot S_{r,d} = S'_{r,d}$ and $\Lambda = 99$ nm$^3$ (case 1), $\Lambda = 144$ nm$^3$ (case 2) and $\Lambda = 189$ nm$^3$ (case 3)—fit lines of all three cases overlapped. All experiments were done in 4M LiCl (buffered at pH~7) under +50 mV of applied voltage (100 kHz lowpass filtering, 250 kHz sampling rate) with ~100 nM hSTf.

with $\gamma \cdot S_{r,d} = S'_{r,d}$ and $\Lambda=99$ nm$^3$ (case 1), $\Lambda=144$ nm$^3$ (case 2) and $\Lambda=189$ nm$^3$ (case 3)—fit lines of all three cases overlapped

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention is directed to improvements to existing small nanopore fabrication (<5 nm) using controlled dielectric breakdown (CDB) and real-time cleaning of the nanopore (without pore enlargement-size preservation). The present inventors used a solution of 1:4.5 sodium hypochlorite (available chlorine 10-15%): 1M KCl (buffered at pH~7) for nanopore fabrication and 1:4.5 sodium hypochlorite (available chlorine 10-15%): 2M LiCl (buffered at pH~7), or 1:4.5 sodium hypochlorite (available chlorine 10-15%): 4M LiCl (buffered at pH~7) solution for nanopore cleaning, that prevents clogging to begin with, or that self-cleaning or easily cleanable with the simple application of a voltage across the membrane.

As used herein the phrase "chemically-tuned controlled dielectric breakdown (CT-CDB) nanopore membrane" refers to adding one or more chemical agents during CDB to tune the nanopore behavior and properties. The CT-CDB allows for long-term stability of measurements in the presence of only electrolyte (open pore current stability) and ability to support many molecular detection events. In addition, the CT-CBD has pore that unclog spontaneously, in response to voltage cessation or application, or both.

The present invention includes one or more of the following advantages. (1) The present invention produces instantaneously Ohmic nanopores without the need for any conditioning steps and without having to wait for a prolonged time (>20 hours) for rectification/self-gating characteristics to minimize. (2) The nanopores of the present invention are less prone to analyte clogging from sticky analytes. For example, DNA could be run through ~4.7 nm diameter pores under +200 mV of applied voltage without clogging for >1 hour (>3000 translocation instances). (3) The present invention allows for real-time visualization of the nanopore cleaning. Other methods are trial-and-error. (4) The present invention allows for cleaning that does not require unmounting of the pore from the holding cell and consist of user-friendly chemicals-ideal for hand-held devices. (5) The present invention unclogs clogged pores from analytes (better than conventional voltage pulse application which leads to pore growth). (6) The present invention also reduces the downtime between experiments caused by the requirement of cleaning to be free-of any residual analytes to <10 minutes. (7) The present invention allows for cleaning that does not change the initial pore characteristics (i.e. size and analyte translocation characteristics). (8) The present invention allows for a prolonged experimental lifetime of the nanopore (for example, tested with the analyte for 7 hours over the course of 5 days and over multiple analyte loading-cleaning cycles).

As used herein, the term "clog-resistant" refers to one or more nanopores that are coated as taught in the present invention that do not clog and/or that are easily unclogged by adding or removing an applied voltage across the nanopores. By using the hypochlorite (or an equivalent oxidizer) to form the nanopore(s), the nanopore(s) formed in the membrane are coated with a monoprotic surface termination that makes the nanopore(s) self-cleaning, that prevent analytes from clogging the nanopore(s), do not attach or bind to the nanopore(s), and/or are easily and consistently cleanable. Surprisingly, it has been found that the monoprotic surface termination allows for very consistent measurements of analytes over extended periods of time. Nanopore(s) of the prior art are found to provide inconsistent measurements over time, are found to exhibit continuously varying pH-dependent conductance, and clog irreversibly. Typical nanopores of the prior art have a general maximum operating time of just 1-10 minutes of use. Using the present invention, it was found that inconsistencies in measurements were greatly reduced or eliminated, and the nanopore(s) were functional for hours. The present nanopore(s) provided consistent measurements after 15, 20, 30, 40, 45, 60, 75, 90, 120, 150, 180 minutes, or for 4, 5, 6, 7, 8, 9, 10, 15, 20, 24, 36, 48, or 60 hours.

Fabrication:

Previously reported CDB methods for small nanopore fabrication use 1M KCl and require soaking of the nanopore for >20 hours in 3.6M LiCl electrolyte solution after the fabrication to obtain ohmic nanopores.[1] Briggs, K.; Kwok, H.; Tabard-Cossa, V., Automated fabrication of 2-nm solid-state nanopores for nucleic acid analysis. *Small* 2014, 10 (10), 2077-2086.

Using the new electrolyte solution of the present invention, the inventors were are able to obtain instantaneous ohmic pores as shown in FIGS. 1A to 1C (diameter of the pore presented here is ~3 nm through a 12 nm thick silicon nitride nanopore). FIGS. 1A to 1C show Current-Voltage (I-V) curves of a nanopore fabricated (~3 nm in diameter) through a 12 nm thick silicon nitride membrane using 1:4.5 sodium hypochlorite (10-15%): 1M KCl (buffered at pH~7) solution. (FIG. 1A) 1M KCl, (FIG. 1B) 2M LiCl and (FIG. 1C) 4M LiCl. All electrolytes are buffered at pH~7 and I-V curves are taken soon after fabrication.

For nanopore fabrication, the present inventors used an electric field 0.7 V/nm. The standard deviation of these open-pore current traces at 0 mV, +200 mV, and +400 mV is about ~36-40 pA. The stable open-pore currents remained the same during experiments (FIG. 2) with no clogging for >1-hour experimental time (>3000 translocation events). Clogging could easily be removed though bleach cleaning (FIG. 3B) nanopore (4M LiCl buffered at pH~7) nanopore under +200 mV applied voltage.

Figure 3A:
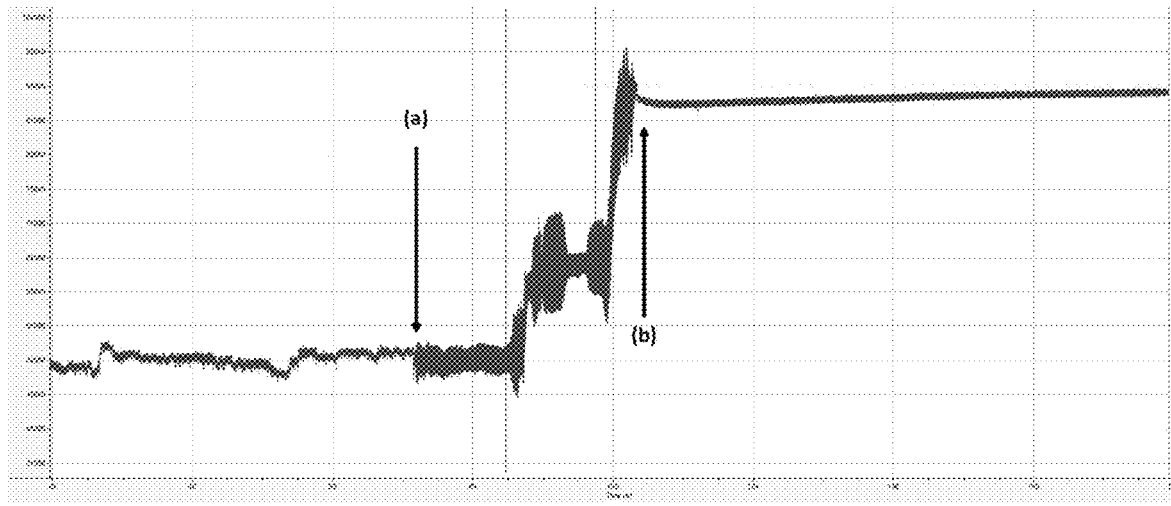
FIG. 3A shows a nanopore cleaned with water after running holo-human serum transferrin (hSTf) through it (2M LiCl at pH~7 under an applied voltage of +400 mV). The baseline is unstable and residual events are present before point (a). The Faraday cage is opened at point (a) to introduce the bleach solution and closed at point (b). A stable baseline free of events is obtained after point (b) and the increase in current is due to the higher conductivity of the bleach solution compared to 2M LiCl.

Cleaning:

A common hurdle is cleaning the nanopore between analyte runs without significantly changing its properties (i.e. size, surface chemistry, and noise). More commonly used methods are (oxygen) plasma cleaning (to remove organic material), immersion in piranha solution or exchanging the content with copious amounts of water and ethanol. The first two approaches typically require unmounting of the nanopore chip from its holding cell and can change its hydrophilicity, but can also be done in situ. The water/ethanol cleaning method is done by exchanging the nanopore content with water, followed by ethanol and then placing the cell under a vacuum. An alternative to this is to use copious amounts of buffer solution (or water) and check the open-pore baseline for any residual analytes (a time-consuming process which usually requires multiple exchange cycles of water and electrolyte). Abelow, A. E.; Schepelina, O.; White, R. J.; Vallée-Bélisle, A.; Plaxco, K. W.; Zharov, I., Biomimetic glass nanopores employing aptamer gates responsive to a small molecule. Chemical Communications 2010, 46 (42), 7984-7986. This is not an effective method as shown in FIG. 3A. On the other hand, there is no guarantee that a versatile commercial device would be built to run a single analyte. Therefore, the present inventors developed a nanopore cleaning step as a key step for the further development of this technology, which is pivotal for use in detections aimed at comparing different analytes in the same pore.

FIG. 3A shows a nanopore cleaned with water after running holo-human serum transferrin (hSTf) through it (2M LiCl at pH~7 under an applied voltage of +400 mV). The baseline is unstable and residual events are present before point (a). The Faraday cage is opened at point (a) to introduce the bleach solution and closed at point (b). A stable baseline free of events is obtained after point (b) and the increase in current is due to the higher conductivity of the bleach solution compared to 2M LiCl.

Figure 3B:
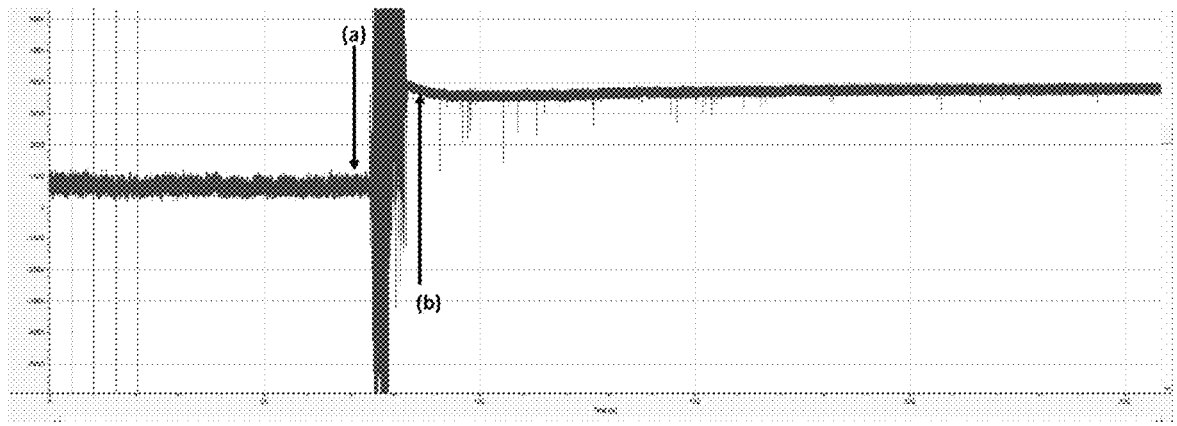
FIG. 3B shows a pore (that shown in FIG. 2) that was clogged during water cleaning (current trace till point (a)) opens up after the introduction of the bleach cleaning (1:4.5 sodium hypochlorite (available chlorine 10-15%): 4M LiCl (buffered at pH~7)) solution (at point (a)). The Faraday cage was open from point (a) to (b). The events start to decrease with time after point (b).

FIG. 3B shows a nanopore (that shown in FIG. 2) that was clogged during water cleaning (current trace till point (a)) opens up after the introduction of the bleach cleaning (1:4.5 sodium hypochlorite (available chlorine 10-15%): 4M LiCl (buffered at pH~7)) solution (at point (a)). The Faraday cage was open from point (a) to (b). The events start to decrease with time after point (b).

Reusability from Cleaning.

Both the cis and trans chambers of the nanopore containing cell are filled with 2M LiCl (pH~7) and after obtaining an I-V curve (for size estimation) holo human serum transferrin (hSTf—used as the test analyte) is loaded to a final concentration of ~250 nM to the cis side of the nanopore. After obtaining a statistically significant data pool (>1000) of current perturbations (plotted as conductance change ($\Delta G$) vs translocation times ($\Delta t$) as shown in FIG. 4C) as a result of the electrophoretic analyte translocations (under an applied voltage of +400 mV), the content of both the wells is exchanged with water. The open-pore current was then acquired after filling with 2M LiCl (pH~7) which shows the presence of the residual analyte. After adjusting the well content to be 1:4.5 bleach: 2M LiCl (pH~7), a voltage of +400 mV was applied for ~60 seconds (FIGS. 3A and 3B) which showed the open-pore current to be free of any residual analyte molecules. The content was exchanged again with 2M LiCl and an I-V curve was obtained. Then hSTf was again loaded to the cis side. This cycle of loading and cleaning was continued for a total of 4 times. The downtime between two analytes runs is reduced to <10 minutes with this new method—a significant improvement from conventional methods which sometimes fails to clean the pore even after numerous cleaning rounds. A near-perfect overlap of the scatter plots of $\Delta G$ vs $\Delta t$ and I-V curves (FIG. 4C and FIG. 4B, respectively) indicate that the cleaning solution does not change the initial pore characteristics. The experiments were conducted for a total of ~7 hours. The near perfect overlap of the scatter plots speaks for the reusability of the nanopore with the current cleaning method.

FIGS. 4A to 4C show: FIG. 4A show a 10-second representative current traces corresponding to four separate runs of hSTf through the same ~26 nm diameter nanopore (in chronological order from top to bottom) in ~30 nm thick silicon nitride membrane. The scale bar in red represents 1 nA. Before each run, the nanopore is cleaned with the cleaning solution described in the text. The I-V curves in (FIG. 4B) corresponding to each run shows a perfect overlap and a similar observation is seen in (FIG. 4C) where scatter plots corresponding to each run also show a near-perfect overlap (run1: magenta, run2: green, run3: black and run4: blue)

Example 1. Improving Solid-State Single-Molecule Sensing Performance, Lifetime, and Analyte Scope for Omics by Targeting Surface Chemistry During Fabrication.

The present invention includes a novel Solid-state nanopores (SSN) fabrication approach that uses a modified nanopore surface chemistry during pore formation, and thus create nanopores in silicon nitride ($SiN_x$) capable of sensing a wide analyte scope-nucleic acid (double-stranded DNA), protein (holo-human serum transferrin) and glycan (malto-dextrin). In contrast to $SiN_x$ pores fabricated without this comprehensive approach, the pores of the present invention are Ohmic, have extremely stable open-pore current during analyte translocation (>1 hour) over a broad range of pore diameters (≲3-~30 nm) with spontaneous current correction (if current deviation occurs), and higher responsiveness (i.e. inter-event frequency) to negatively charged analytes (~6.5× in case of DNA). These pores were fabricated by modifying CDB with a chemical additive-sodium hypochlorite—that resulted in dramatically different nanopore surface chemistry including ~3 orders of magnitude weaker $K_a$ compared to CDB pores which is inextricably linked with significant improvements in nanopore performance with respect to CDB pores.

The present inventors sought to simultaneously tune nanopore size and surface chemistry, with the explicit goal of targeting a range of molecule classes. The inventors wanted to preserve the best of controlled dielectric breakdown (CDB) in terms of ease of use and size tunability, while easing the downstream application challenges to conventional $SiN_x$ pores. As a starting point, the inventors wanted to first improve even upon simple platform challenges such as open pore current stability and clogging. In the end, the inventors wanted to establish whether chemical conditioning during fabrication could yield a type of $SiN_x$ nanopore that had better performance. Specifically, the inventors wanted reliable performance during sensing without the need for cumbersome or elusive amelioration steps; such reliable performance across a range of analyte classes encompassing wide-ranging molecular properties would be an even more compelling outcome especially with the footprint of nanopore technology expanding beyond DNA sequencing. To that end, the inventors hypothesized that by adding chemically reactive species to the CDB electrolyte, it would be possible to modify the resulting nanopore surface chemistry as a part of the formation. The novel method of the present invention is the chemically-tuned CDB (CT-CDB). As an example sodium hypochlorite (NaOCl) was tested. Whereas dilute NaOCl solutions have been reported to degrade nanopore quality during cleaning,[15] the work presented here shows a complex interplay between NaOCl and the applied voltage whereby the combination of the two produce improved nanopore qualities that individual components alone are not (even remotely) able to produce. NaOCl is only used for the fabrication of pores, which is then flushed with copious amounts of water followed by the electrolyte of interest in which biomolecule translocation experiments are carried out. Such extensive flushing is required to ensure the nanopore environment is free of NaOCl, which could potentially oxidize biomolecules.

The inventors selected three distinct biological analytes to include the molecule classes underpinning genomics, proteomics, and glycomics. Aside from whether or not a single type of $SiN_x$ nanopore could operate reliably across this highly varied analyte scope, each analyte offered unique characteristics for challenging and assaying the nanopore, itself. Double-stranded DNA (dsDNA) is negatively charged, maltodextrin is charge-neutral, and holo-human serum transferrin protein (hSTf) is amphoteric.[4] The inventors used the dsDNA for pore sizing[14, 16] and assessing its responsiveness, maltodextrin for assaying the nanopore surface chemistry and electrokinetic mechanism of sensing, and hSTf for larger diameter pore assessment. All analytes were used to assess pore reliability. This is the first time where such a broad range of biomolecules with such significantly different size, charge, electrokinetic transport and, electrostatic properties have been used for characterization and performance evaluation of a nanopore fabrication protocol.

The target platform was SSN formed in thin-film (~10-12 nm-thick) $SiN_x$ membranes, with diameters ranging from sub-5 nm to ~30 nm. For dsDNA, the pore size range of ~3-5 nm is preferred since such smaller pore sizes allow the discrimination of short homopolymers and sub-nanometer structural changes of DNA.[17, 18] For maltodextrin ~5 nm diameter pores were preferred over larger pores so that the assay would be more sensitive to the surface effects of interest. For example, previous work has shown that electroosmosis is necessary to drive translocation of such an uncharged molecule through a nanopore, and this only happens when the nanopore surface is charged.[3] The analyte electrophoresis (EP) and nanopore surface electroosmosis (EO) can be opposing or reinforcing, depending on the fixed surface charge polarity. $SiN_x$ nanopores have been used previously for protein profiling[13, 19-22] and unlike DNA, they are not uniformly charged. Here, the inventors used hSTf as a test molecule to investigate the suitability of the CT-CDB method to fabricate larger diameter pores: exceedingly difficult with CDB due to non-opening failure among other factors.[23]

Figure 5A:
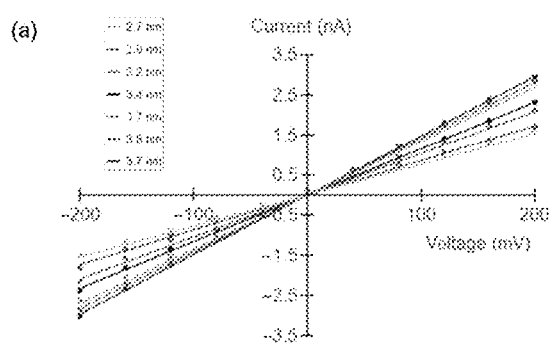
FIGS. 5A to 5D show.
Figure 5B:
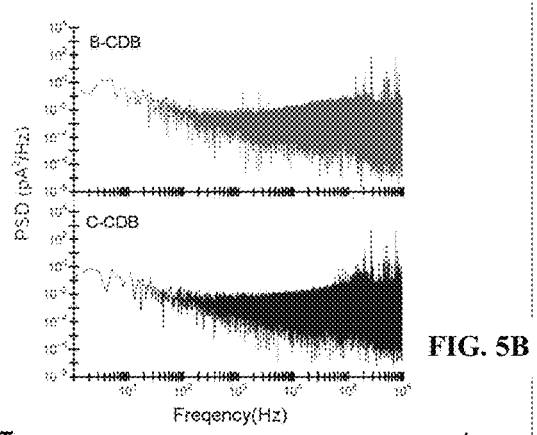
Figure 5C:
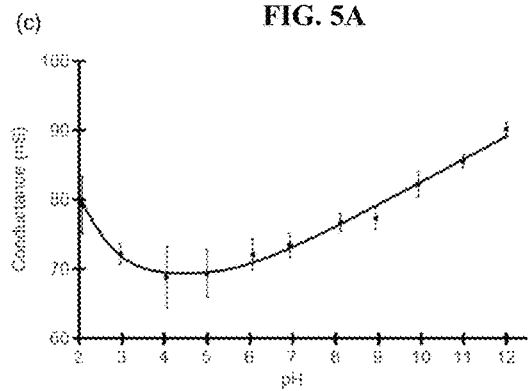
Figure 5D:
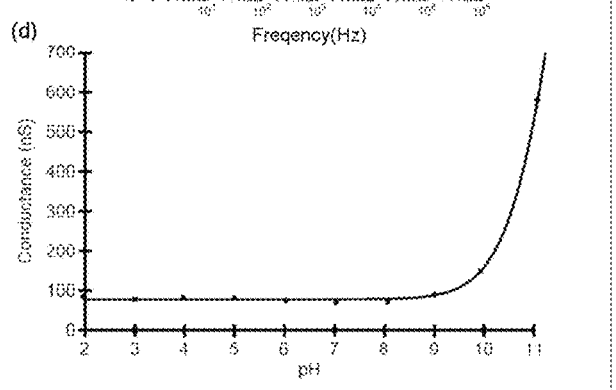
Figures 7A, 7B, 7C, 7D:
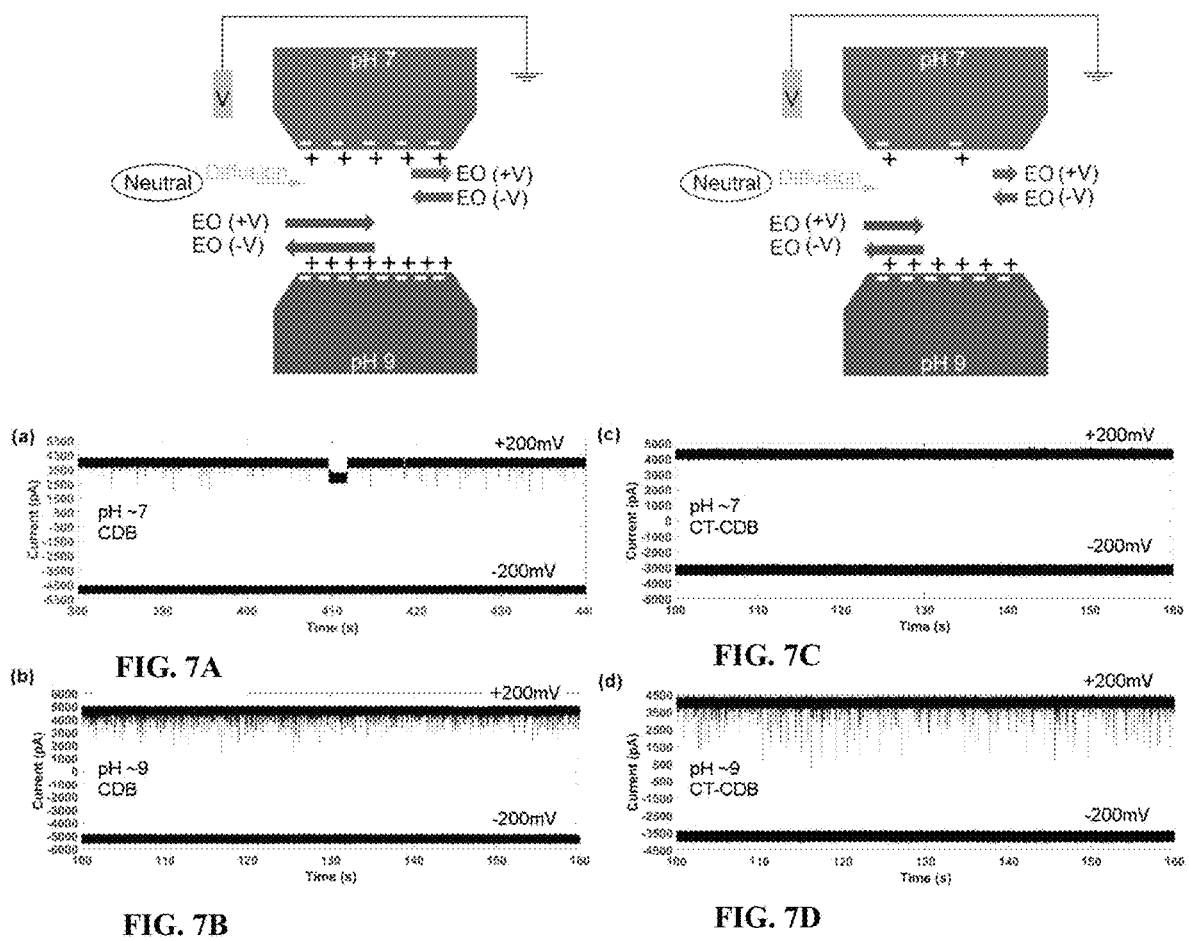
Figures 8A, 8B, 8C, 8D:
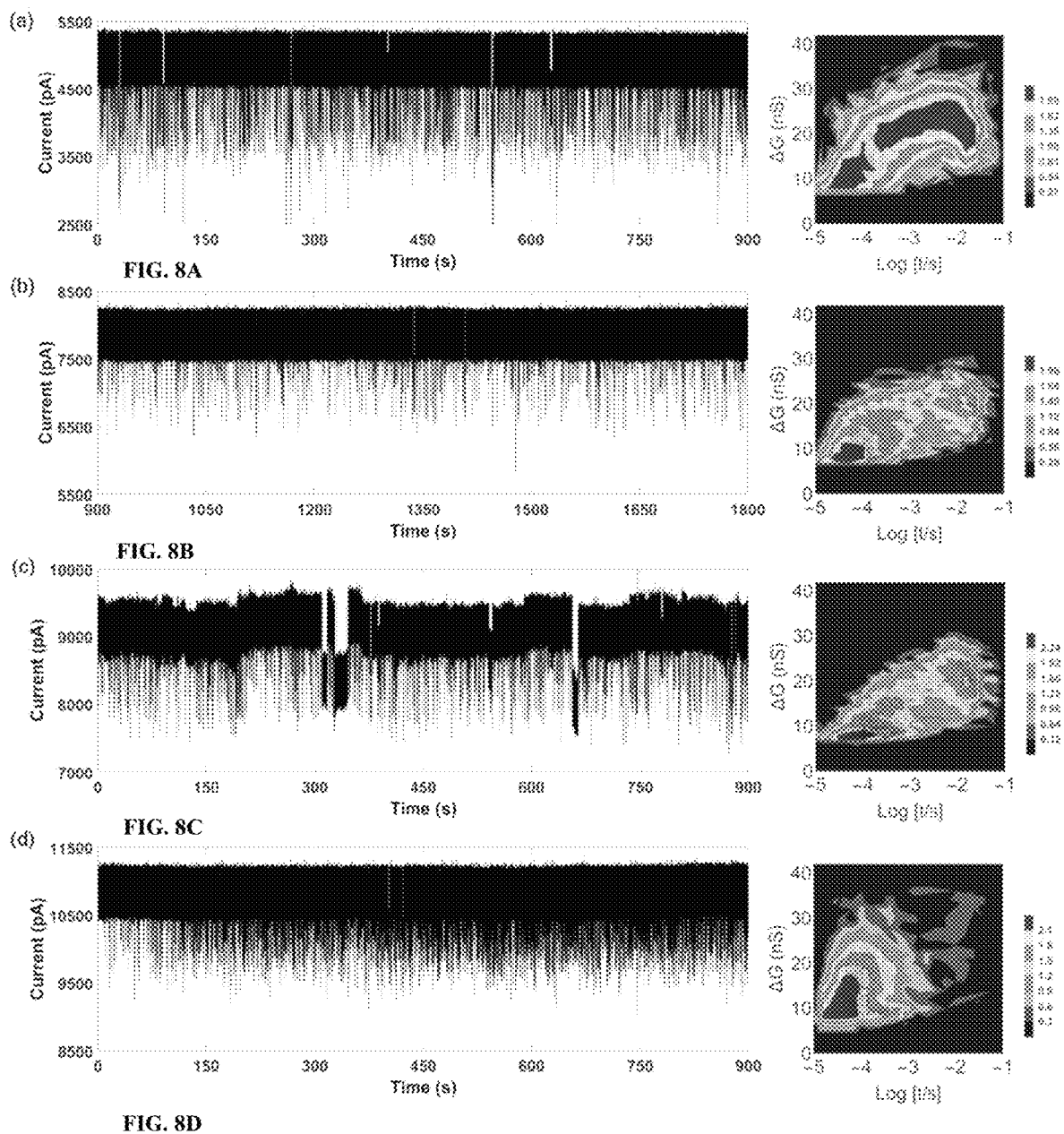

CT-CDB nanopores were quickly Ohmic (measured after 10-40 minutes of soaking), even in the small, <4 nm diameter range as shown by FIG. 5A. This contrasts favorably with the need for overnight soaking or for voltage conditioning as has been reported for CDB pores. Overall, CDB and CT-CDB pores showed similar noise characteristics as a function of frequency at pH ~7 as shown in FIG. 5B. The two pore classes, however, showed dramatically different conductance behavior as the solution pH was changed (FIGS. 5C and 5D). Nanopore conductance, G, depends on the nanopore surface charge, σ, (Equation S1), which can be pH-dependent. Due to the sensitivity of nanopore G to changes in (nanopore) surface charge density as a function of pH (due to protonation or deprotonation of surface head groups), G-pH surveying has gained traction recently as a tool to probe the surface chemistry of nanopores.[14, 16, 26] Additionally, such probing can be carried out soon after the fabrication, does not require any exotic sample preparation steps, and are more convenient over conventional microscopic methods (e.g. energy-dispersive X-ray spectroscopy (EDS)) which are also challenged by access to the nanopore inner surface, the extremely small length scale of the pores, and the likelihood of electron- or ion-induced changes to the pore structure during imaging. Amphoteric CDB $SiN_x$ pores have a minimum in conductance at the isoelectric point (4.3±0.4, 3 unique pores, mean±standard deviation), with larger current magnitudes when they are charged.[14, 16, 26] In contrast, the G-pH trend of the CT-CDB pores, is characteristic of a surface where a single type of acidic surface group is present. Fitting this data using Equations S1 and S2, the inventors obtained 10.1±0.2, 10.1±3.1 $nm^{-2}$ and 450.7±44.7 $F/m^2$ for $pk_a$, Γ (density of surface chargeable groups) and $C_{eff}$ (effective Stern layer capacity) respectively for CT-CDB nanopores. This $K_a$ is ~3 orders of magnitude weaker than that obtained for $SiN_x$ pores by CDB, and is responsible for the much later onset of the surface conductance increase in these CT-CDB pores.[14, 16] Qualitatively, the CT-CDB pores display a similar surface chemistry to those fabricated by the Tesla-Coil Assisted method (TCAM)—a salt-free fabrication method—and hydroxyl functionalized nanopores.[14, 16] That is, the nanopore G of them are plateaued at lower pH values and then rises with increasing pH (resembles FIG. 5D) unlike amphoteric $SiN_x$ (FIG. 5C).

Given the apparent change in $SiN_x$ nanopore surface chemistry when formed by CT-CDB, the inventors wanted to first test whether the nanopores still supported analyte translocation. The inventors used the most familiar analyte for nanopore sensing, DNA, to confirm translocation, to size the pore, and to benchmark CT-CDB pore performance versus CDB pores. Even though the literature suggests dsDNA experiments are done over long time periods (hours sometimes), the (representative) current traces are 100 seconds at best[12] where changes to the open-pore current, if present, are largely invisible (FIGS. 9A and 9B). The instability of nanopores in solution-pore growth over time—has been acknowledged in the literature.[27, 28] Occasional drops in current signals (of CT-CDB) due to analyte sticking have been observed to be self-corrected almost instantaneously (FIG. 10A to 10C). To add to the repertoire of beneficial properties for longer sensing experiments, the inventors have noticed that if a given CT-CDB pore clogs and the open-pore current is not self-corrected, it could be unclogged by briefly zeroing the voltage and then re-applying the initial applied voltage for sensing to continue the experiment (FIG. 10A to 10C)—the clogging may perhaps be due to a weak interaction of the analyte and the pore-opening.

To place this unclogging behavior in context, single-stranded polynucleotides typically translocate through $SiN_x$ nanopores at an average speed of ~1 nucleotide/µs (at 150 mV voltage bias).[29] To resolve individual bases, it is estimated that this translocation rate should be ~1 nucleotide/ms or slower. At this desired rate, to sequence the 6 billion base pairs long diploid mammalian genome in 50,000 bases long ssDNA fragments (after denaturing the dsDNA) with only a single translocation pass would require, without multiplexing, a single pore to be open for >2000 hours. Even with an array of >500 nanopore channels, it would require ~48 hours.[30] Even though the scope of this work is not DNA sequencing, the stable CT-CDB open-pore currents, such as the ~2.5 hours of current trace shown in FIG. 11A to 11C, should greatly benefit SSN-based efforts for sequencing (the same pore was used for >8 hours of experimentation yielding ~48,500 events over multiple dsDNA concentrations and applied voltages-over multiple experiments—and was still open and stable when decommissioned). This open-pore current stability may also become a positive key aspect where a set of comparative experiments are expected to be conducted using the same nanopore to minimize intra and inter pore size variations.[3, 4] In this work, for nanopores fabricated using the CT-CDB protocol, show (steady) representative continuous current traces as shown in FIG. 6A (and zoomed in image in FIG. 6B) that are 1800 seconds long—the longest continuous trace in the literature-pertaining to dsDNA translocating through a ~3.4 nm diameter pore. The inventors attempted to translocate dsDNA through a similar sized pore fabricated from the CDB protocol but were met with continuous analyte-sticking which eventually leads to irreversible pore-clogging before any substantial number of events could be collected. The signal characteristics using CT-CDB pores are well-behaved in comparison to the CDB standard. Three distinct populations of conductance blockage magnitude (FIG. 6C, 12A to 12C) are consistent with non-translocation (i.e. collision) events ($\Delta G_0$), translocation of linearized DNA (AGA and DNA exhibiting different folded-over conformations ($\Delta G_2$).[12] A detailed analysis and discussion are provided in SI Section 6. In spite of the different CT-CDB versus CDB surface chemistry and the very different propensity of the two pores to clog, measured conductance blockage provide evidence for translocation through CT-CDB pores.

FIGS. 6A to 6D show: (FIG. 6A) A ~30-minute current of 1 kb dsDNA (25 nM) translocating through a ~3.4 nm diameter CT-CDB pore in 4 M LiCl (buffered at pH~7) and (FIG. 6B) a 30-second representative current trace of (FIG. 6A) from 100 s to 130 s. The experiment was conducted over 3 hours at +200 mV of applied voltage, 250 kHz sampling rate and 100 kHz lowpass filtering. (FIG. 6C). Scatter plot (13417 events over 3 hours) showing conductance change ($\Delta G$) and the log of translocation time. (FIG. 6D) Calibration curve (inter-event frequency vs dsDNA concentration) constructed by adding 1 kb dsDNA (4M LiCl buffered at pH~7) in ~5 nM increments to ~5 nm diameter nanopores fabricated from the CDB protocol (magenta) and CT-CDB protocol (black). Each dsDNA aliquot of (FIG. 6D) was run for at least 900 seconds and each data point represents at least ~750 (CDB) and 3800 (CT-CDB) events. Data were obtained using an applied voltage of +200 mV, 250 kHz of sampling frequency and 100 kHz of low-pass filtering.

The change to nanopore surface chemistry naturally gives rise to the question of whether CDB and CT-CDB $SiN_x$ sensing performance was different.[31] The inventors were interested in the throughput of $SiN_x$ nanopores—not just by minimizing clogging, but by their analyte responsiveness measured by resistive pulse rate. The inventors constructed the calibration curves in FIG. 2d—each data point represents the mean and the standard deviation of the inter-event frequency from 6 trials per fabrication protocol (2 pores per fabrication protocol, 3 trials each). Given the appreciable overlap of the PSD, resistive pulse identification was performed on both pores with the same blockage magnitude threshold (see Resistive Pulse Characterization section under Methods for more details). The slopes of the CDB and CT-CDB protocols were 0.028 $s^{-1}$ $nM^{-1}$ and ~0.18 $s^{-1}$ $nM^{-1}$ respectively which clearly indicated the pores fabricated from the CT-CDB protocol to be ~6.5 times more sensitive to 1 kb dsDNA compared to those fabricated from CDB protocol. In another experiment using a ~10.0 nm diameter CT-CDB pore (dsDNA concentration ~83 nM), the inventors obtained ~$2 \times 10^5$ events (214,353) in ~80 minutes-equivalent to translocation of ~0.2 billion base pairs in total. The inventors tested two more unique nanopores to reproducibly test the ability of the CT-CDB pores to cross the $2 \times 10^5$ event limit and they yielded 210,000 (pH~7) and 270,000 (pH~6) events respectively. This qualitatively showcases the throughput of CT-CDB nanopores and thereby its potential to increase the statistical significance in data collection.

FIG. 7A to 7D shows representative 60-second current traces of maltodextrin translocation in response to +200 mV and −200 mV (current and voltage polarities are of identical sign) in pores fabricated from (FIG. 7A) and (FIG. 7B) the CDB and (FIG. 7C) and (FIG. 7D) CT-CDB protocols at pH ~7 (upper row) and ~9 (lower row). The schematic representation above the current traces summarizes the EO direction at each instance. All data were acquired at 250 kHz sampling rate, 100 kHz lowpass filtering using ~5 nm diameter pores that are nominally ~12 nm in thickness. The scatter plots corresponding to these traces are shown in FIGS. 13A and 13B.

To probe the surface charge of the nanopore further than is possible with G-pH measurements, the inventors used maltodextrin—a charge-neutral polysaccharide. Voltage-driven nanopore translocation cannot occur by electrophoresis when the analyte is uncharged, only by EO. If resistive pulses are detected, the corresponding voltage polarity required for EO can then be used to identify the nanopore surface charge polarity. The surface charge of CDB $SiN_x$ nanopores is known to be net negative at pH ~7 and ~9, so that with analyte on the trans side of the nanopore, events would be expected in response to a +200 mV applied voltage on the trans side, and no events would be expected at −200 mV. The experimental results confirmed this expectation. The same set of experiments were repeated with a CT-CBD pore. Events were detected using a +200 mV applied voltage, with no events observed at −200 mV. The CT-CBD surface charge that was indicated by the G-pH curve was thus confirmed through neutral glycan detection by EO that could arise only with a charged nanopore surface (see the schematic representation in FIG. 3). In addition, given the applied voltage polarity necessary for EO, the CT-CDB surface charge polarity could be identified as negative. It is worthwhile noting the meager event frequency of maltodextrin through the CT-CDB pore at pH~7 (compared to the CDB pore) because the pore surface (of CT-CDB) is expected to be near-neutral at this pH. The higher event frequencies at each pH using CDB pores support the charge density magnitudes determined from fitting the G-pH curves—~3.7 events $s^{-1}$ at pH ~7 (−0.078 $C/m^2$) and ~19.9 events $s^{-1}$ at pH ~9 (−0.17 $C/m^2$) compared to 0.16 events $s^{-1}$ (−0.0013 $C/m^2$) and 11.2 events $s^{-1}$ (−0.13 $C/m^2$) at the two respective pH values using CT-CDB (the surface charge density at each pH is indicated in parentheses).

The findings of surface charge polarity using the glycan are useful for understanding the frequency of events in the earlier DNA sensing case. In those experiments at pH ~7, the positive voltage polarity for DNA translocation by EP would face an opposing EO driving force because of the negative surface polarity of both CDB and CT-CDB pores. Given the greater charge density on the surface of CDB pores, however, the event frequency of DNA detection in these pores would be expected to be lower than for the CT-CDB pores where the EO was reduced by the near-neutral surface charge. In addition, the higher negative charge on CDB would result in higher electrostatic repulsion with the DNA rendering CDB pores to have a lower event frequency. The alignment between nanopore surface charge polarity and analyte charge polarity will dictate whether a particular analyte will be more frequently detected under particular experimental conditions in a CDB pore or a CT-CDB pore. As shown in FIGS. 5A to 5D, the magnitude of the nanopore surface charge density can be tuned by solution pH. The pH response of nanopore surface charge can also be tuned through, for example, chemical vapor deposition,[32] atomic layer deposition,[33] and surface-chemical attachment methods such as silanization[31] and photo-hydrosylilation.[14] These techniques either require specialized tools or a synthetic organic palette. With CDB gaining a substantial footprint in the nanopore community, the inventors' method provides a robust and efficient (both time and cost-wise) surface treatment solution to produce favorable analyte translocation characteristics.

Figure 14:
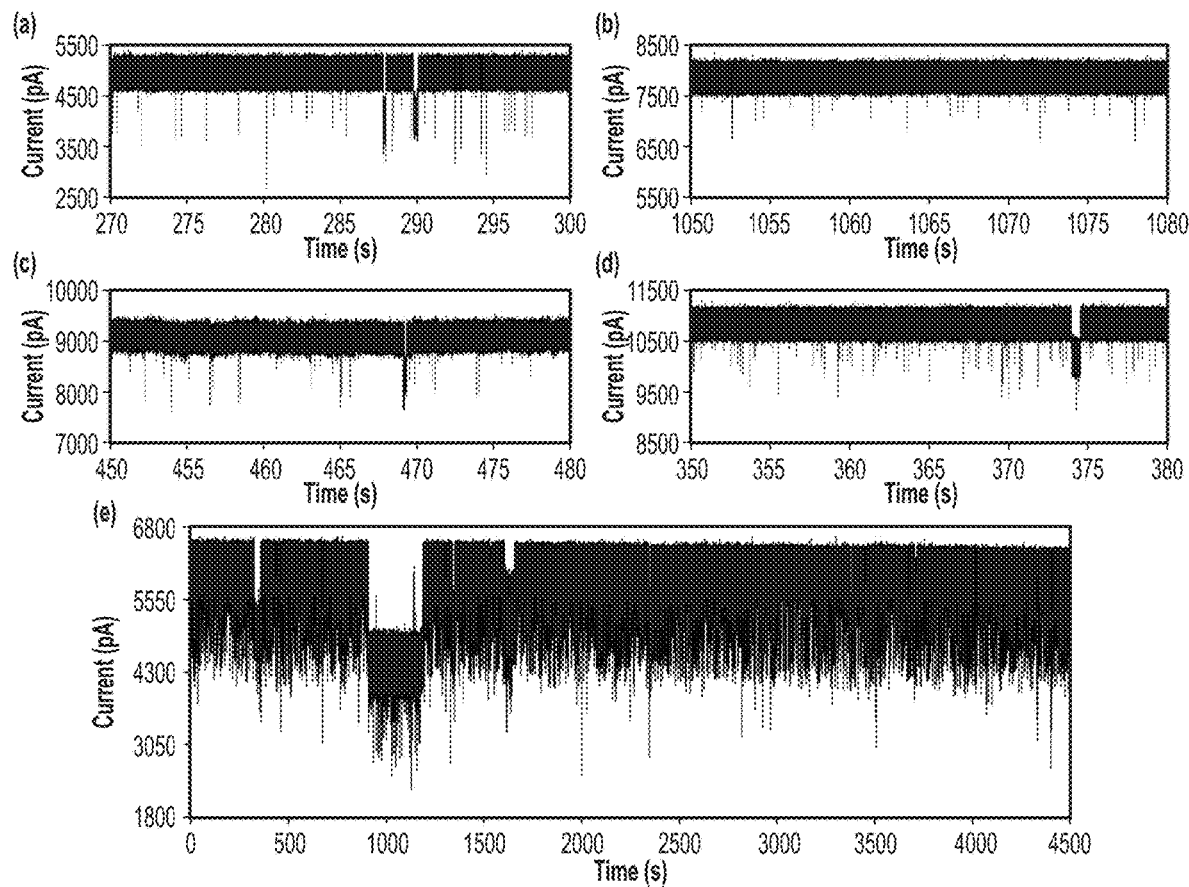
Figure 15:
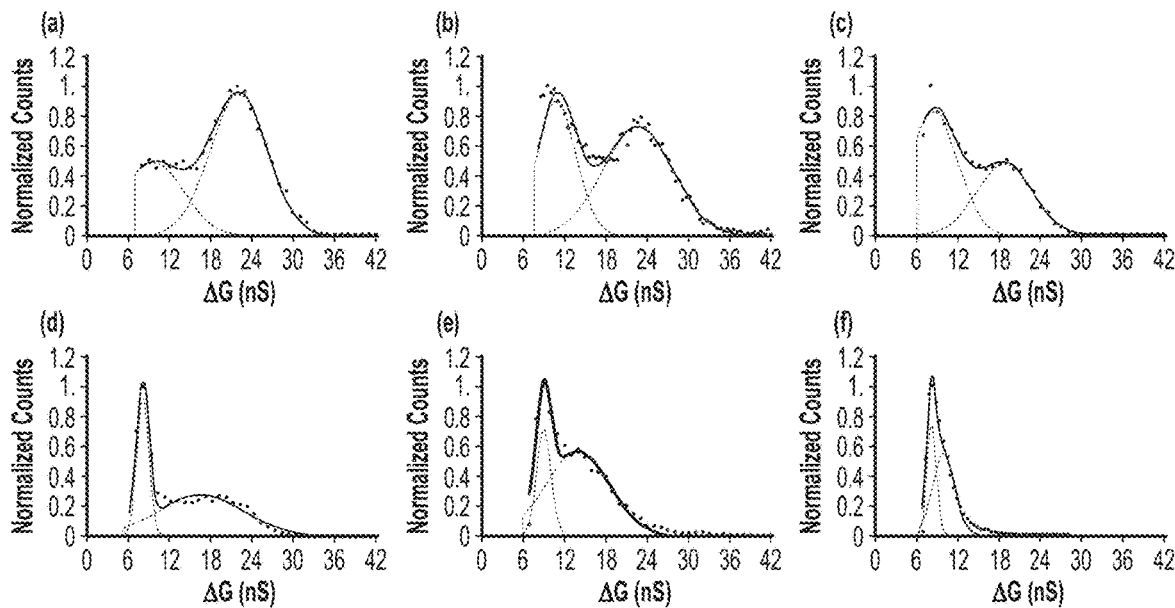

So far, the inventors have discussed the fabrication of nanopores with <10 nm in diameter. However, to date, fabricating larger diameter pores with CDB is exceedingly difficult (due to non-opening failure among other factors as noted previously)[23] and the inventors note that CT-CDB allowed us to fabricate pores as large as ~30 nm in <10 minutes (using an electric field strength of ~0.76 V/nm). Unlike the previous set of experiments where the open-pore diameter was in the coveted ≤5 nm diameter regime (apart from few exceptions demonstrated in the SI for comparison purposes)—the nanopore surface effects are more pronounced on the analyte translocation due to the comparative size of the nanopore and the analyte in question—the pores used in this section are much larger (compared to the analyte) and thus provides an opportunity to qualitatively observe the impact surface charge would have on analyte translocation in such pore diameter regimes. The CT-CDB pores used herein are also quickly ohmic (i.e. rectification ~1) and possess the favorable qualities discussed earlier like their smaller diameter counterparts (evident by FIGS. 8A to 8D and FIGS. 14A to 14E). In the inventors' previous work with hSTf (with a molecular weight of 80 kDa and a molecular radius of ~3.3 nm)—an important iron carrier—the inventors had demonstrated the voltage-induced unfolding of proteins and to minimize the likelihood of this phenomenon, the inventors operated at no more than +50 mV.[34] The zeta potential of hSTf at pH~7 is reported to be negative, and given the CT-CDB pore surface has a near-neutral net negative charge at pH ~7, there would be a weak EO opposing the translocation by EP that is not sufficient to hinder the analyte travel in the electrophoretic sense. Given the higher surface charge density, the EO will be more pronounced in CDB pores resulting a lower event frequency than in CT-CDB. The protein was added to the cis side to a final concentration of ~100 nM (2.5× more dilute than in the inventors' previously reported work)[4] and applied +50 mV to the trans side. The event frequency of negatively charged hSTf through CDB pores (~0.3 events/second) was insufficient to collect statistically significant data pool (>1000 events) within a reasonably rapid timeframe. Thus, the concentration of hSTf was increased up to ~250 nM (>2 events/second—comparable to that from CT-CDB pores at the 100 nM level). Some representative current traces of hSTf in CT-CDB and CDB are shown in FIGS. 14A to 14E. To further elaborate the exceptional baseline stability associated with CT-CDB nanopore, the inventors ran a ~13.8 nm diameter nanopore, without any user supervision for ~75 minutes where the pore self-corrected any transient clogs and remained open as seen in FIG. 14E—the longest continuous protein translocation trace in the literature.

As described above CT-CDB pore-clogging was self-corrected when working with DNA. The ~10 nm diameter CT-CDB pore had frequent yet reversible clogs that could be similarly removed either by zeroing the voltage or by a single zap—a commonly used ≤50 ms application of ~1.3 V. The instances where unclogging could be done by zeroing the voltage could point to a weak interaction of the protein with the pore opening rather than sticking within. The larger diameter pores could largely be run without such interruptions. The heatmaps, as seen in FIG. 4, showed two distinct populations. Even though the heatmap corresponding to ~20 nm diameter CT-CDB pore (FIG. 8D) resembled a single population, the ΔG histogram of it (FIG. 15E) showed two distinct populations. Therefore, all histograms corresponding to the ΔG profiles were fitted with two Gaussian functions (FIGS. 15A to 15F). The first population, considering the span of the translocation time, may correspond to collisions with the pore opening and interestingly, the mean of the first Gaussian population (lower ΔG distribution termed $\Delta G_{p,c}$) did not change appreciably (FIG. 16A; ~8.4 nS to ~10.7 nS) with the pore diameter unlike that of the second population as seen in FIG. 16B. The second population (higher ΔG distribution termed $\Delta G_{p,f}$) is attributed to protein translocations. The $\Delta G_{mf}$ from CT-CDB pores of ~10-30 nm in diameter were then fitted with Equation S6 (see SI section 10 for fitting details) using the literature reported volume for hSTf (144±45 nm³).[35] The corresponding fit lines are shown in FIG. 16B.

FIGS. 8A to 8D show: (column 1) Representative 15 minute current traces originating translocation of hSTf in 4M LiCl (buffered at pH~7) under +50 mV applied voltage (100 kHz lowpass filtering, 250 kHz sampling rate) and their (column 2) corresponding heatmaps overlaid with raw-data points of conductance change as a function of translocation time of (FIG. 8A) ~12 nm diameter CT-CDB pore, (FIG. 8B) ~17 nm diameter CT-CDB pore, (FIG. 8C) ~18 nm diameter CDB pore and (FIG. 8D) ~20 nm diameter CT-CDB pore. For brevity, representative 30-second current traces of each of these pores are shown in FIGS. 14A to 14E.

Controlled dielectric breakdown (CDB) in the presence of a chemical agent to modify nanopore surface chemistry during pore fabrication is here introduced as chemically-tuned controlled dielectric breakdown (CT-CDB). Using a single chemical additive, sodium hypochlorite, nanopores of ~5,3 to 30 nm in diameter through ~10-12 nm-thick silicon nitride ($SiN_x$) membranes could be fabricated. The pores were easily wetted, Ohmic without lengthy equilibration or conditioning times, and presented stable open-pore currents in the presence and absence of the analytes of interest. The fundamental effect of CT-CDB was to improve the nanopore surface chemistry from the classic amphoteric surface chemistry of conventional $SiN_x$ nanopores to monoprotic surface termination-without a chemical functionalization step separate from the CDB fabrication, and with the inorganic surface coating integral to the membrane. This new class of $SiN_x$ nanopore allowed for long sensing times consistently beyond what is generally reported in the literature: DNA traces >8 hours (~48,500 individual single-molecule events across multiple analyte concentrations and voltages) and protein traces as long as ~75 minutes, absent any user intervention. Open-pore currents remained steady for long measurement times, would frequently and consistently unclog spontaneously, with the removal of an applied voltage or, less frequently, in response to a reversal of the sensing voltage polarity. In addition to a steady pore current over longer times, the CT-CDB pores had a 6.5× greater sensitivity to DNA than CDB pores. CT-CDB is thus a simple, single-step fabrication, conditioning-free, and surface tuning method (without an added organic layer) that produce instantaneously ohmic pores over a wide range of pore diameters conducive for a range of analyte classes by overcoming hurdles such as analyte-sticking and open-pore current drift while preserving all positive qualities of CDB which consequently has the potential to appreciably encourage further studies and applications in nanopore science.

Nanopore Fabrication: Pore fabrication was done with <1 V/nm of transmembrane electric field strength, as is typical for CDB using the custom-circuit outlined in the work of Kwok et al. through nominally ~10 nm (NX5002Z), ~11 nm (NBPX5001Z-HR), ~12 nm (NBPX5001Z-HR) thick free-standing $Si_xN_y$ membranes purchased from Norcada, Canada submerged in 1M KCl (P9333, Sigma-Aldrich) buffered at pH~7 (10 mM HEPES (4-(2-hydroxyethyl)-1-piperazineethanesulfonic acid) purchased from Sigma-Aldrich (H0527))—CDB—or a blend of 2:9 (v:v) 1M KCl: sodium hypochlorite (425044, Sigma Aldrich)—CT-CDB. Preliminary changes of this ratio from 2:9 were not immediately promising during the exploratory phase. For fabrication of <5 nm (diameter) nanopores, the electric field strength was set to <0.7 V/nm and for larger pore fabrication, higher field strengths were used. After the fabrication, the content was exchanged with 4M LiCl (213233, Sigma Aldrich) buffered at pH~7 (10 mM tris buffer (J61036, Fisher Scientific)) to obtain current-voltage (I-V) curves. These were obtained after equilibration in 4 M LiCl buffered at pH~7 for at least ~10 minutes, but no more than ~40 minutes. I-V curves were obtained using a custom-coded LabVIEW (version 2016, National Instruments) program by ramping the voltage from −200 mV to +200 mV and the pore size was estimated using Equation 51 and S2. The rectification of the fabricated nanopores was calculated as the ratio of conductance at positive voltage regime ($G_+$) to that at negative voltage regime ($G_-$): $G_+/G_-$. The pores depicted in FIG. 5A to 5D showed a $G_+/G_-$ of 1.01±0.02—indicating the absence of rectification. Polydimethylsiloxane (86435K43, McMaster-Carr) gaskets were used to mounted nanopore chip between two custom-built polytetrafluoroethylene (PTFE) flow half-cells. All electrical signals were obtained using Ag/AgCl electrodes.

Analyte Sensing Conditions.

All dsDNA experiments were done in 4 M LiCl (buffered at pH~7 using tris buffer), under an applied voltage of +200 mV, with a sampling frequency of 250 kHz and low-pass filtering of 100 kHz. dsDNA was added to the cis side (typically ~25 nM unless otherwise noted) and, perturbations to the open-pore current as a result of analyte translocation was characterized using depth (ΔI), duration (δt) of the resistive pulse (see methods for further details) and inter-event frequency (f).

For maltodextrin, 1 M KCl is used as the electrolyte and data were acquired at a sampling frequency of 250 kHz and 100 kHz of lowpass filtering. Maltodextrin was added to the trans side (same as voltage application side) at a final concentration of 13 μM.

For hSTf, 4 M LiCl (buffered at pH~7 using tris buffer), applied voltage of +50 mV, with a sampling frequency of 250 kHz and low-pass filtering of 100 kHz was used. It was added to the cis side to a final concentration of ~250 nM (CDB pores) or ~100 nM (CT-CDB pores).

pH-Conductance Curves: 1 M KCl buffered at pH~7 (10 mM HEPES) was used as the electrolyte. The pH was adjusted by adding HCl (H1758, Sigma-Aldrich) or KOH (306568, Sigma-Aldrich) dropwise and the pH was measured using an Orion Star™ pH meter.

Power Spectral Density (PSD) curves: These were generated using MATLAB (version 9.4) using the inbuilt fft function. For each PSD, a 2-second current representative trace was extracted from nanopores submerged in 4M LiCl buffered at pH~7 using +200 mV of applied voltage, 250 kHz sampling frequency and 100 kHz lowpass filtering.

Biomolecule Preparation: dsDNA (Ser. No. 10/787,018, Fisher Scientific), holo-human serum transferrin (T0665, Sigma Aldrich) and maltodextrin (419680, Sigma Aldrich). dsDNA was used as supplied. Stock solutions of hSTf and maltodextrin were prepared by dissolving them in ultra-pure water (ARS-102 Aries high purity water systems or Synergy UV Millipore Ultrapure water system) with a resistivity of >18 MΩ cm to a final concentration of ~2.5 μM and ~1.7 mM (0.2% w/v), respectively. The stock solution of hSTf and maltodextrin were stored at ~4° C. and used within 7 days.

Electrical Measurements: Axopatch 200B (Molecular Devices LLC, USA) was used to acquire all current traces at a sampling frequency of 250 kHz with 100 kHz low pass filtering. Signal was digitized using a Digitizer 1440A (Molecular Devices LLC, USA) while instrument control was done using Clampex software (version 10.7.0.3, Molecular Devices LLC, USA). Signal digitization for I-V curves was done using a BNC 2110 (National Instruments, USA) while instrument control was done using custom LabVIEW scripts (Version 15, National Instruments). Ag/AgCl electrodes were used for all signal acquisition purposes.

Resistive Pulse Characterization: Custom-written scripts of MATLAB (version 9.4) was used for dsDNA, maltodextrin, and hSTf event analysis. Events were classified as current perturbations at-least five times the standard deviation of the baseline current ($I_0$). Each event was then characterized in terms of amplitude (I), duration and change in conductance $$\left(\Delta G = \frac{I_0 - I}{V}\right).$$

Characterization of Pore Diameter and Surface Charge Density.

The diameter of the fabricated nanopores and their surface charge density were estimated using, $$G = K\left(\frac{1}{\frac{\pi r_0^2}{L} + \frac{\mu|\sigma|}{K} - \frac{2\pi r_0}{L}} + \frac{2}{\alpha \cdot 2r_0 + \beta \cdot \frac{\mu|\sigma|}{K}}\right)^{-1} = \quad \text{Eq. S1}$$

$$\left(\frac{1}{G_{bulk} + G_{surface}} + \frac{1}{G_{access}}\right)^{-1}$$

where G, K, L, $r_0$, σ, μ, α and β are the ionic conductance, electrolyte conductivity, nanopore length, nanopore radius, nanopore surface charge density, surface counterion mobility, and model-dependent parameters (both set to 2) respectively.[1, 2] The nanopores were fabricated either using the method outlined by Kwok et al. with conventional electrolyte 1 M KCl[3] (buffered at pH ~7 using 10 mM HEPES) or 2:9 bleach:1 M KCl (with ~10 mM HEPES at pH ~7) mixture (modified method) and the size was estimated using Equation 1. The σ of Equation 51 can be approximated as,[2, 4]

$$|\sigma| \cong \frac{C_{eff}}{\beta e} W\left(\frac{\beta e}{C_{eff}} \exp((pH - pK_a)\ln(10) + \ln(e\Gamma))\right) \quad \text{Eq. S2}$$

where e, Γ, $PK_a$, β, $C_{eff}$, and W is the elementary charge, number of surface chargeable groups, the dissociation constant of those groups, inverse of the thermal energy, effective Stern layer capacitance, and Lambert W function respectively.

Characterization of Pore Diameter and Surface Charge Density.

The diameter of the fabricated nanopores and their surface charge density were estimated using, $$G = K \left( \frac{1}{\frac{\pi r_0^2}{L} + \frac{\mu|\sigma|}{K} - \frac{2\pi r_0}{L}} + \frac{2}{\alpha \cdot 2r_0 + \beta \cdot \frac{\mu|\sigma|}{K}} \right)^{-1} = \qquad \text{Eq. S1}$$

$$\left( \frac{1}{G_{bulk} + G_{surface}} + \frac{1}{G_{access}} \right)^{-1}$$

where G, K, L, $r_0$, $\sigma$, $\mu$, $\alpha$ and $\beta$ are the ionic conductance, electrolyte conductivity, nanopore length, nanopore radius, nanopore surface charge density, surface counterion mobility, and model-dependent parameters (both set to 2) respectively.[1,2] The nanopores were fabricated either using the method outlined by Kwok et al. with conventional electrolyte 1 M KCl[3] (buffered at pH ~7 using 10 mM HEPES) or 2:9 bleach:1 M KCl (with ~10 mM HEPES at pH ~7) mixture (modified method) and the size was estimated using Equation 1. The σ of Equation 51 can be approximated as,[2,4]

$$|\sigma| \cong \frac{C_{eff}}{\beta e} W\left( \frac{\beta e}{C_{eff}} \exp((pH - pK_a)\ln(10) + \ln(e\Gamma)) \right) \qquad \text{Eq. S2}$$

where e, Γ, $pK_a$, β, $C_{eff}$, and W is the elementary charge, number of surface chargeable groups, the dissociation constant of those groups, inverse of the thermal energy, effective Stern layer capacitance, and Lambert W function respectively.

Representative Current Traces of CDB Nanopores.

FIGS. 9A and 9B show: (top row) Extended representative current traces and (bottom row) representative 100-second current traces in CDB nanopores resulting from dsDNA translocation through (FIG. 9A) ~4.6 nm and (FIG. 9B) ~6.2 nm diameter CDB nanopore. All translocation experiments were done in 4 M LiCl buffered at pH~7, 250 kHz acquisition rate, 100 kHz low-pass filtering, +200 mV applied voltage with a final dsDNA concentration of ~25 nM.

With extended current traces, the drift of the open-pore current associated with CDB nanopores is clear as seen in FIGS. 9A and 9B. However, with 100-second current traces, these are largely invisible. This drifting behavior has been observed on a consistent basis. The inventors noted that the severity of open-current drift behavior increases with increasing pore diameter. The quality of the baseline also deteriorates with increasing pore size in the case of CDB nanopores. However, CT-CDB nanopores show exceptional baseline stability as seen in FIGS. 6A to 6D and FIG. 11A to 11C. Section 3: CT-CDB Nanopore Current Behavior in Response to Unclogging Strategies; Passive Spontaneous Self-Correction, Active Voltage Zeroing & Opposite Voltage Bias.

FIGS. 10A to 10C show: All translocation traces presented here are from 25 nM dsDNA in 4M LiCl buffered at pH~7 (250 kHz sampling frequency and 100 kHz lowpass filtering) through CT-CDB pores. (FIG. 10A) A ~4.9 nm pore that self corrects after an initial clog, (FIG. 10B) a ~4.0 nm diameter pore that failed to self-correct was recovered by zeroing the voltage and (FIG. 10C) a ~4.9 nm diameter pore unclogged by applying −200 mV. The baseline voltage is +200 mV except in (FIG. 10B) where it is +150 mV and for comparison, after unclogging the pore, it is run at +200 mV for a short while. CT-CDB pores maintained overall current level stability by spontaneous correction, and by more active interventions including temporary cessation of applied voltage, and temporary voltage polarity reversal.

FIGS. 10A to 10C show the unclogging strategies that the inventors followed in this work for CT-CDB with some representative instances from dsDNA runs. Nanopores used to characterize holo-hSTf showed very similar behavior (not shown). However, if a CT-CDB pore clogs irreversibly such that the open-pore current is not recovered spontaneously or by a passive 0 V period, attempts to unclog with higher voltage pulses (≥0.8 V/nm-higher than the electric field used for initial pore formation) using the CDB apparatus and conventional CDB electrolyte led to adverse pore enlargement (this is also true for CDB pores). Such enlargement has been previously observed (with analyte-free pores) and beneficially used for pore conditioning.5

Representative Current Traces of CT-CDB Nanopores.

FIGS. 11A to 11C shows representative current traces of 4.3 nm diameter CT-CDB pore corresponding to translocation of ~25 nM dsDNA at (FIG. 11A)+100 mV, (FIG. 11B)+150 mV and (FIG. 11C)+200 mV applied voltage. All translocation experiments were done in 4M LiCl (buffered at pH ~7), 250 kHz sampling rate and 100 kHz lowpass filtering. Reversible clogging at +150 mV is equivalent to those observed in FIGS. 10A to 10C.

In FIGS. 11A to 11C, the pore was run continuously for ~4.4 hours and yielded 19645 resistive pulses (cumulative from all three applied voltages) before it clogged and the open-pore current could not be recovered by unclogging strategies outlined in section 3. Thus the inventors resorted to the more conventional method of exchanging the well content with copious amounts of water after which the open-pore current was recovered-no change in pore diameter was observed. The pore was then used to obtain 3 of the 6 trials of the calibration curve presented in FIGS. 6A to 6D resulting in a total experimental time of ~8.2 hours and 48,500 events—the pore diameter only increased by a meager ~0.3 nm.

Histograms and Gaussian Fitting Corresponding to dsDNA Translocations.

The histograms corresponding to ΔG in FIGS. 12A to 12C were developed using the built-in Histogram function of Mathematica 11.0.1.0 with a custom bandwidth of 0.05 nS. Each of the distributions was then fitted with Gaussian functions, each in the form, $$A_i \exp(-(\Delta G - \mu_i)^2 / \sigma_i^2) \qquad \text{Eq. S3}$$

where $A_i$, $\mu_i$, $\sigma_i$ and ΔG is the amplitude, the mean and standard deviation of the $i^{th}$ Gaussian function and change in conductance respectively. The fitting was done with the inbuilt function Nonlinear-model-fit of Mathematica in Automatic mode. The individual Gaussians are shown in dashed (black) lines and the cumulative is shown in the solid (black) line.

Interpretation of Histograms of dsDNA Translocations

The assignment of collisions in FIG. 14A was further strengthened through the diminishing of this population when larger diameter pores were used (FIG. 14B and FIG. 14C). The change in conductance as a result of dsDNA passage ($\Delta LG_{dsDNA}$) can be modelled using, $$\Delta G_{dsDNA} = G - K \left( \frac{\frac{1}{\pi r_{with\ DNA}^2} + \frac{\mu |\sigma|}{K} \cdot \frac{2\pi r_0}{L} + \frac{\mu}{K} \cdot \frac{q_{\lambda\text{-}DNA}}{L}}{\alpha \cdot 2 r_{with\ DNA} + \beta \frac{\mu |\sigma|}{K}} \right)^{-1}$$ Eq. S4 where $r_{with\ DNA} = \sqrt{r_0^2 - r_{dSDNA}^2}$ and $q_{\lambda\text{-}DNA}$ been effective linear charge density of lambda-DNA. For a ~3.4 nm diameter pore (through a nominally 11 nm thick membrane submerged in 4 M LiCl with a conductivity of 17.4 S/m) and considering the widely reported values for the hydrated radius of dsDNA (i.e. ranging from 1.1-1.3 nm),[6-8] the expected ΔG from Equation S1 would range from ~8.6 to ~10.8 nS. Thus, the experimentally observed value from FIG. 12A (~10.2 nS) is bracketed by the predicted value range of Equation S4.

FIGS. 12A to 12C show scatter plots (1st row) and histograms of ΔG (2nd row) as a result of dsDNA translocating through (a) ~3.4 nm, (b) ~4.7 nm and (c) ~10.0 nm diameter CT-CDB nanopores. All translocation experiments were done in 4 M LiCl (buffered at pH ~7), +200 mV of applied voltage, 250 kHz sampling rate and 100 kHz lowpass filtering. The histograms were fitted with (a) three (b) three (c) and two Gaussian functions.

Scatter Plots Corresponding to Maltodextrin Translocations.

FIGS. 13A and 13B show scatter plots of change in conductance (ΔG) vs the log of translocation time (t) corresponding maltodextrin translocating through pores fabricated from (top row) CDB and (bottom row) CT-CDB protocols. Experiments were conducted at (a) pH ~7 using +200 mV and (b) pH ~9 using +200 mV with 250 kHz sampling frequency and 100 kHz lowpass filtering.

Representative Current Traces Corresponding to hSTf Translocations.

FIGS. 14A to 14E show representative 30-second current traces of hSTf translocations through (FIG. 14A) ~11.9 nm CT-CDB pore, (FIG. 14B) 17.2 nm CT-CDB pore, (FIG. 14C) 17.9 nm CDB pore and (FIG. 14D) 20.4 nm CT-CDB pore. (FIG. 14E) Extended current trace of ~75 minutes through a ~13.8 nm CT-CDB pore. All experiments were done in 4M LiCl (buffered at pH~7) under +50 mV of applied voltage (100 kHz lowpass filtering, 250 kHz sampling rate) with ~100 nM hSTf except in (FIG. 14C) where the concentration was ~250 nM.

Histograms and Heat Maps Corresponding to hSTf Translocations.

The change in conductance (ΔG) histograms shown in FIGS. 15A to 15F was constructed using a custom bin width of 1 nS and subsequently fitted with the formula $$\phi_{fit} = \frac{1}{2}(1-\theta)\Sigma_{i=1}^2 A_i \exp(-(\Delta G - \mu_i)^2 / \sigma_i^2)$$ Eq. S5 where $A_i$, $\mu_i$, $\sigma_i$ and ΔG is the amplitude, the mean and standard deviation of the $i^{th}$ Gaussian function and change in conductance respectively. The step function, $(1-\theta)$, was set to 1 when $\Delta G > \Delta G_{min} - B_{width}$, where $\Delta G_{min}$ and $B_{width}$ are the minimum ΔG and bin width. Otherwise, it was set to 0. The peak of lower ΔG and higher ΔG populations in FIGS. 15A to 15F will be assigned as $\Delta G_{p,c}$ and $\Delta G_{p,f}$ respectively.

FIGS. 15A to 15F show histograms corresponding to the conductance change (ΔG) as result of hSTf translocating through (FIG. 15A) ~11.9 nm CT-CDB pore, (FIG. 15AB) ~13.8 nm CDB pore, (FIG. 15C) 17.2 nm CT-CDB pore, (FIG. 15AD) 17.9 nm CDB pore, (FIG. 15AE) 20.4 nm CT-CDB pore and (FIG. 15F) 27.8 nm CT-CDB pore. The inset shows the corresponding heatmaps overlaid with the scatter plots of ΔG vs translocation time. All experiments were done in 4M LiCl (buffered at pH~7) under +50 mV of applied voltage (100 kHz lowpass filtering, 250 kHz sampling rate) with ~100 nM hSTf except in (FIG. 15AD) where the concentration was ~250 nM.

$\Delta G_p$ of hSTf with CT-CDB Pore Diameter.

The hSTf data collected from CT-CDB ~10-28 nm diameter pores, provides us the opportunity to model the change in open-pore conductance (as a result of protein translocation ($\Delta G_p$)) as a function of open-pore radius ($r_0$), $$\Delta G_p = K \frac{\gamma \cdot \Lambda}{(L + 1.6 r_0)^2} S_{r,d}$$ Eq. S6

Where Λ, γ, and $S_{r,d}$ are transiently excluded electrolyte volume, the shape factor and the correction factor, The γ for a globular protein is assumed to be 1.5 for spheres.[9] Even though the inventors assumed voltage-driven protein unfolding to be minimal at +50 mV, it would be absent conclusively at 0 mV. Thus, to minimize any uncertainty associated with γ due to voltage driven unfolding (even if it is negligible), the inventors coupled γ with $S_{r,d}$ ($\gamma \cdot S_{r,d} = S'_{r,d}$). Then, using the literature reported Λ range for hSTf (144±45 nm³), the inventors fitted the $\Delta G_p$ collected from CT-CDB ~10-28 nm diameter pores with $S'_{r,d}$ as the sole free parameter using Λ=99 nm³ (case 1), Λ=144 nm³ (case 2) and Λ=189 nm³ (case 3). The $S'_{r,d}$ for each of the cases (from the fit) was ~5.7, ~3.9 and ~3.0 respectively. All three fits, as shown in FIG. 16B overlapped.

FIGS. 16A and 16B shows: (FIG. 16A) $\Delta G_{p,c}$ and (FIG. 16B) $\Delta G_{p,f}$ as a function of pore diameter of nanopores fabricated from the CT-CDB protocol. The vertical and horizontal error bars are the error in the Gaussian fit (3×) and error originating from membrane thickness uncertainty (±2 nm, provided by the manufacturer) respectively. The solid-line in (b) is a fit made using equation S6 with $\gamma \cdot S_{r,d} = S'_{r,d}$ and Λ=99 nm³ (case 1), Λ=144 nm³ (case 2) and Λ=189 nm³ (case 3)—fit lines of all three cases overlapped. All experiments were done in 4M LiCl (buffered at pH~7) under +50 mV of applied voltage (100 kHz lowpass filtering, 250 kHz sampling rate) with ~100 nM hSTf.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Karawdeniya, B. I.; Bandara, Y. N. D.; Nichols, J. W.; Chevalier, R. B.; Hagan, J. T.; Dwyer, J. R.; Testing, Challenging Nanopores with Analyte Scope and Environment. Journal of Analysis 2019, 3 (1), 61-79.
2. Dwyer, J.; Bandara, Y.; Whelan, J.; Karawdeniya, B.; Nichols, J., Silicon Nitride Thin Films for Nanofluidic Device Fabrication. Nanofluidics 2016, 41, 190.
3. Karawdeniya, B. I.; Bandara, Y. N. D.; Nichols, J. W.; Chevalier, R. B.; Dwyer, J. R., Surveying silicon nitride nanopores for glycomics and heparin quality assurance. Nat. Commun. 2018, 9 (1), 3278.
4. Saharia, J.; Bandara, Y. N. D.; Goyal, G.; Lee, J. S.; Karawdeniya, B. I.; Kim, M. J., Molecular-Level Profiling of Human Serum Transferrin Protein through Assessment of Nanopore-Based Electrical and Chemical Responsiveness. ACS Nano 2019, 13 (4), 4246-4254.
5. Graf, M.; Liu, K.; Sarathy, A.; Leburton, J.-P.; Radenovic, A., Transverse Detection of DNA in a MoS2 Nanopore. Nature Nanotechnology 2015, 10, 1070-1077.
6. Kasianowicz, J. J.; Brandin, E.; Branton, D.; Deamer, D. W., Characterization of individual polynucleotide molecules using a membrane channel. Proceedings of the National Academy of Sciences 1996, 93 (24), 13770-13773.
7. Astier, Y.; Braha, 0.; Bayley, H., Toward single molecule DNA sequencing: direct identification of ribonucleoside and deoxyribonucleoside 5-monophosphates by using an engineered protein nanopore equipped with a molecular adapter. Journal of the American Chemical Society 2006, 128 (5), 1705-1710.
8. Lee, J. S.; Saharia, J.; Bandara, Y. N. D.; Karawdeniya, B. I.; Goyal, G.; Darvish, A.; Wang, Q.; Kim, M. J.; Kim, M. J., Stiffness measurement of nanosized liposomes using solid-state nanopore sensor with automated recapturing platform. Electrophoresis 2019, 40 (9), 1337-1344.
9. Darvish, A.; Lee, J. S.; Saharia, J.; Sundaram, R. V. K.; Goyal, G.; Bandara, N.; Ahn, C. W.; Kim, J.; Dutta, P.; Chaiken, I., Mechanical characterization of HIV-1 with a solid-state nanopore sensor. Electrophoresis 2018.

10. Freedman, K. J.; Ahn, C. W.; Kim, M. J., Detection of long and short DNA using nanopores with graphitic polyhedral edges. ACS Nano 2013, 7 (6), 5008-5016.
11. D. Y. Bandara, Y. M. N.; Tang, J.; Saharia, J.; Rogowski, L. W.; Ahn, C. W.; Kim, M. J., Characterization of Flagellar Filaments and Flagellin through Optical Microscopy and Label-Free Nanopore Responsiveness. Analytical Chemistry 2019, 91 (21), 13665-13674.
12. Kwok, H.; Briggs, K.; Tabard-Cossa, V., Nanopore fabrication by controlled dielectric breakdown. PLoS One 2014, 9 (3), e92880.
13. Yusko, E. C.; Johnson, J. M.; Majd, S.; Prangkio, P.; Rollings, R. C.; Li, J.; Yang, J.; Mayer, M., Controlling protein translocation through nanopores with bio-inspired fluid walls. Nature Nanotechnolagy 2011, 6 (4), 253-260.
14. D. Y. Bandara, Y. M. N.; Karawdeniya, B. I.; Hagan, J.; Chevalier, R.; Dwyer, J. R., Chemically Functionalizing Controlled Dielectric Breakdown Silicon Nitride Nanopores by Direct Photohydrosilylation. ACS Appl. Mater. Interfaces 2019.
15. Ando, G.; Hyun, C.; Li, J.; Mitsui, T., Directly observing the motion of DNA molecules near solid-state nanopores. ACS Nano 2012, 6 (11), 10090-10097.
16. Bandara, Y. N. D.; Karawdeniya, B. I.; Dwyer, J. R., Push-Button Method To Create Nanopores Using a Tesla-Coil Lighter. ACS Omega 2019, 4 (1), 226-230.
17. Venta, K.; Shemer, G.; Puster, M.; Rodriguez-Manzo, J. A.; Balan, A.; Rosenstein, J. K.; Shepard, K.; Drndic, M., Differentiation of short, single-stranded DNA homopolymers in solid-state nanopores. ACS Nano 2013, 7 (5), 4629-4636.
18. Singer, A.; Kuhn, H.; Frank-Kamenetskii, M.; Meller, A., Detection of urea-induced internal denaturation of dsDNA using solid-state nanopores. J. Phys.: Condens. Matter 2010, 22 (45), 454111.
19. Firnkes, M.; Pedone, D.; Knezevic, J.; Doblinger, M.; Rant, U., Electrically facilitated translocations of proteins through silicon nitride nanopores: conjoint and competitive action of diffusion, electrophoresis, and electroosmosis. Nano Lett. 2010, 10 (6), 2162-2167.
20. Plesa, C.; Kowalczyk, S. W.; Zinsmeester, R.; Grosberg, A. Y.; Rabin, Y.; Dekker, C., Fast translocation of proteins through solid state nanopores. Nano Lett. 2013, 13 (2), 658-63.
21. Han, A.; Schtirmann, G.; Mondin, G.; Bitterli, R. A.; Hegelbach, N. G.; de Rooij, N. F.; Staufer, U., Sensing protein molecules using nanofabricated pores. Appl. Phys. Lett. 2006, 88 (9), 093901.
22. Cressiot, B.; Oukhaled, A.; Patriarche, G.; Pastoriza-Gallego, M.; Betton, J.-M.; Auvray, L. c.; Muthukumar, M.; Bacri, L.; Pelta, J., Protein transport through a narrow solid-state nanopore at high voltage: experiments and theory. ACS Nano 2012, 6 (7), 6236-6243.
23. Yanagi, I.; Akahori, R.; Takeda, K.-i., Stable fabrication of a large nanopore by controlled dielectric breakdown in a high-pH solution for the detection of various-sized molecules. Scientific Reports 2019, 9 (1), 1-15.
24. Briggs, K.; Kwok, H.; Tabard-Cossa, V., Automated fabrication of 2-nm solid-state nanopores for nucleic acid analysis. Small 2014, 10 (10), 2077-2086.
25. Beamish, E.; Kwok, H.; Tabard-Cossa, V.; Godin, M., Precise control of the size and noise of solid-state nanopores using high electric fields. Nanotechnology 2012, 23 (40), 405301.
26. Hoogerheide, D. P.; Garaj, S.; Golovchenko, J. A., Probing surface charge fluctuations with solid-state nanopores. Physical review letters 2009, 102 (25), 256804.
27. Charron, M.; Briggs, K.; King, S.; Waugh, M.; Tabard-Cossa, V., Precise DNA Concentration Measurements with Nanopores by Controlled Counting. Analytical Chemistry 2019.
28. Briggs, K.; Madej ski, G.; Magill, M.; Kastritis, K.; de Haan, H. W.; McGrath, J. L.; Tabard-Cossa, V., DNA translocations through nanopores under nanoscale pre-confinement. Nano Letters 2017, 18 (2), 660-668.
29. Branton, D.; Deamer, D. W.; Marziali, A.; Bayley, H.; Benner, S. A.; Butler, T.; Di Ventra, M.; Garaj, S.; Hibbs, A.; Huang, X., The potential and challenges of nanopore sequencing. In Nanoscience And Technology: A Collection of Reviews from Nature Journals, World Scientific: 2010; pp 261-268.
30. Bowden, R.; Davies, R. W.; Heger, A.; Pagnamenta, A. T.; de Cesare, M.; Oikkonen, L. E.; Parkes, D.; Freeman, C.; Dhalla, F.; Patel, S. Y., Sequencing of human genomes with nanopore technology. Nat. Commun. 2019, 10 (1), 1869.
31. Anderson, B. N.; Muthukumar, M.; Meller, A., pH tuning of DNA translocation time through organically functionalized nanopores. ACS Nano 2012, 7 (2), 1408-1414.
32. Asatekin, A.; Gleason, K. K., Polymeric nanopore membranes for hydrophobicity-based separations by conformal initiated chemical vapor deposition. Nano Letters 2010, 11 (2), 677-686.
33. Chen, P.; Mitsui, T.; Farmer, D. B.; Golovchenko, J.; Gordon, R. G.; Branton, D., Atomic layer deposition to fine-tune the surface properties and diameters of fabricated nanopores. Nano Letters 2004, 4 (7), 1333-1337.
34. Freedman, K. J.; Jurgens, M.; Prabhu, A.; Ahn, C. W.; Jemth, P.; Edel, J. B.; Kim, M. J., Chemical, thermal, and electric field induced unfolding of single protein molecules studied using nanopores. Anal. Chem. 2011, 83 (13), 5137-5144.
35. Welch, S., Transferrin: the iron carrier. CRC Press: 1992.

What is claimed is:

1. A method of making one or more controlled-size nanopores in a membrane comprising:
providing a SixNy membrane; and
submerging the SixNy membrane in a buffered solution comprising Group IA-Cl or F: Group IA-hypochlorite in the presence of less than or equal to 1 V/nm of transmembrane electric field strength using two electrodes separated by the SixNy membrane.

2. The method of claim 1, wherein a thickness of the SixNy membrane is nominally 5, 6, 7, 8, 9, 10, 11, 12, 13, 15, 20, 25, 30, 35, 40, 50, 60, 70, 75, 80, 90, or 100 nm.

3. The method of claim 1, further comprising adjusting a voltage, or a time, to create nanopores having an average diameter of about 4, 5, 6, 7, 8, 9, 10, 12, 14, 15, 17, 20, or 25 nm.

4. The method of claim 1, wherein the electric field strength is set to <0.7, 0.8, or 0.9 V/nm.

5. The method of claim 1, further comprising changing the electrical rectification characteristic of the nanopores as a ratio of conductance at positive voltage regime (G+) to that at negative voltage regime (G−): G+/G−.

6. The method of claim 1, wherein at least one of: the one or more nanopores are clog-resistant, or the one or more nanopores are unclogged by adding or removing an applied voltage across the one or more nanopores.

7. The method of claim 1, wherein at least one of: the Group IA-Cl or F is buffered prior to the addition of the hypochlorite;

the Group IA-Cl or F is selected from LiCl, NaCl, KCl, RbCl, CsCl, LiF, NaF, KF, RbF, or CsF; or the Group IA-hypochlorite is selected from LiOCl, NaOCl, KOCl, RbOCl, or CsOCl.

8. A chemically-tuned controlled dielectric breakdown (CT-CDB) nanopore membrane comprising:
an $Si_xN_y$ membrane wherein a surface at or about one or more nanopores in the $Si_xN_y$ membrane comprises a monoprotic surface termination.

9. The membrane of claim 8, wherein a thickness of the $Si_xN_y$ membrane is nominally 5, 6, 7, 8, 9, 10, 11, 12, 13, 15, 20, 25, 30, 35, 40, 50, 60, 70, 75, 80, 90, or 100 nm.

10. The membrane of claim 8, wherein the one or more nanopores have an average diameter of about 4, 5, 6, 7, 8, 9, 10, 12, 14, 15, 17, 20, or 25 nm.

11. The membrane of claim 8, wherein the one or more nanopores are formed with an electric field strength set to <0.7, 0.8, or 0.9 V/nm.

12. The membrane of claim 8, wherein at least one of: the one or more nanopores are clog-resistant, or the one or more nanopores are uncloggable by removal or addition of an applied voltage across the membrane.

13. A method of detecting an analyte, comprising:
providing a first chamber and a second chamber, wherein the first and second chamber are separated by an $Si_xN_y$ membrane wherein a surface at or about one or more nanopores in the $Si_xN_y$ membrane comprises a monoprotic surface termination;
placing the analyte in the first or second chamber;
applying a voltage across the $Si_xN_y$ membrane; and
detecting the analyte as it contacts or traverses the $Si_xN_y$ membrane.

14. The method of claim 13, wherein the analytes are selected from nucleic acids, proteins, carbohydrates, molecules, lipids, viruses, liposomes, or nanoparticles.

15. The method of claim 13, wherein a thickness of the $Si_xN_y$ membrane is nominally 5, 6, 7, 8, 9, 10, 11, 12, 13, 15, 20, 25, 30, 35, 40, 50, 60, 70, 75, 80, 90, or 100 nm.

16. The method of claim 13, wherein the one or more nanopores have an average diameter of about 4, 5, 6, 7, 8, 9, 10, 12, 14, 15, 17, 20, or 25 nm.

17. The method of claim 13, wherein the one or more nanopores are formed with an electric field strength set to <0.7, 0.8, or 0.9 V/nm.

18. The method of claim 13, further comprising changing the electrical rectification characteristic of the nanopores as a ratio of conductance at positive voltage regime (G+) to that at negative voltage regime (G−): G+/G−.

19. The method of claim 13, wherein at least one of: the one or more nanopores are clog-resistant, or wherein the one or more nanopores are unclogged by adding or removing an applied voltage across the $Si_xN_y$ membrane.

20. An apparatus comprising:
a membrane having at least one controlled-size nanopore in the membrane between opposing surfaces of the membrane, wherein the membrane is a chemically-tuned controlled dielectric breakdown (CT-CDB) nanopore membrane comprising: an $Si_xN_y$ membrane wherein a surface at or about the at least one controlled-size nanopore comprises a monoprotic surface termination;
a first reservoir and a second reservoir on opposite sides of the at least one controlled-size nanopores;
first and a second electrodes arranged on opposite sides of the fluidic pore of the membrane; and
a controller connected to each of the first and second electrodes and a sensor in fluid communication with at least one of the first and second reservoirs.

* * * * *